United States Patent
Chen et al.

(10) Patent No.: US 11,992,536 B2
(45) Date of Patent: May 28, 2024

(54) DUAL-TARGETING COMPOUND AND PREPARATION METHOD AND APPLICATION THEREOF

(71) Applicant: YANTAI LANNACHENG BIOTECHNOLOGY CO., LTD., Shandong (CN)

(72) Inventors: Xiaoyuan Chen, Shandong (CN); Pengfei Xu, Shandong (CN); Xiaoming Wu, Shandong (CN); Zhide Guo, Shandong (CN); Qingbao Yang, Shandong (CN); Xuejun Wen, Shandong (CN)

(73) Assignee: YANTAI LANNACHENG BIOTECHNOLOGY CO., LTD., Shandong (CN)

( * ) Notice: Subject to any disclaimer, the term of this patent is extended or adjusted under 35 U.S.C. 154(b) by 0 days.

(21) Appl. No.: 18/546,989

(22) PCT Filed: Dec. 9, 2022

(86) PCT No.: PCT/CN2022/137823
§ 371 (c)(1),
(2) Date: Aug. 18, 2023

(87) PCT Pub. No.: WO2023/098920
PCT Pub. Date: Jun. 8, 2023

(65) Prior Publication Data
US 2024/0131205 A1    Apr. 25, 2024

(30) Foreign Application Priority Data
Sep. 29, 2022 (CN) .......................... 202211201081.2

(51) Int. Cl.
*A61K 51/00* (2006.01)
*A61K 47/55* (2017.01)
(Continued)

(52) U.S. Cl.
CPC .......... *A61K 51/0497* (2013.01); *A61K 47/55* (2017.08)

(58) Field of Classification Search
CPC .............................. A61K 51/0497; A61K 47/55
See application file for complete search history.

(56) References Cited

FOREIGN PATENT DOCUMENTS
| CN | 111699181 A | 9/2020 |
| CN | 113164630 A | 7/2021 |

(Continued)

OTHER PUBLICATIONS

International Search Report (with English translation) and Written Opinion issued in PCT/CN2022/137823, dated Apr. 12, 2023, 12 pages provided.

(Continued)

*Primary Examiner* — Michael G. Hartley
*Assistant Examiner* — Melissa J Perreira

(74) *Attorney, Agent, or Firm* — HSML P.C.

(57) ABSTRACT

The present disclosure relates to the fields of nuclear medicine and molecular imaging, and specifically relates to a dual-targeting compound and a preparation method and application thereof. The dual-targeting compound has the following structure shown in Formula (I). The present disclosure also provides a dual-targeting compound capable of being labeled with a radionuclide, and the compound has the following structure shown in Formula (I-1) or Formula (I-2). The dual-targeting compound of the present disclosure has high affinity for an FAP target and an integrin $\alpha_v\beta_3$ target, can realize synergistic targeting of the FAP target and the integrin $\alpha_v\beta_3$ target in tumors, and has high uptake in tumors and long retention time in tumors. The present disclosure also provides a radionuclide labeled dual-targeting compound based on the dual-targeting compound, and a preparation method and application thereof in preparation of medicines for diagnosis or therapy of diseases characterized by overexpression of FAP and/or integrin $\alpha_v\beta_3$.

(I)

Formula (I-1)

(Continued)

-continued

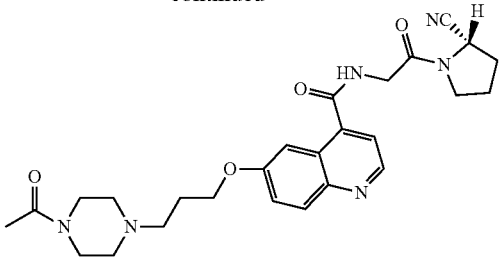

Formula (I-2)

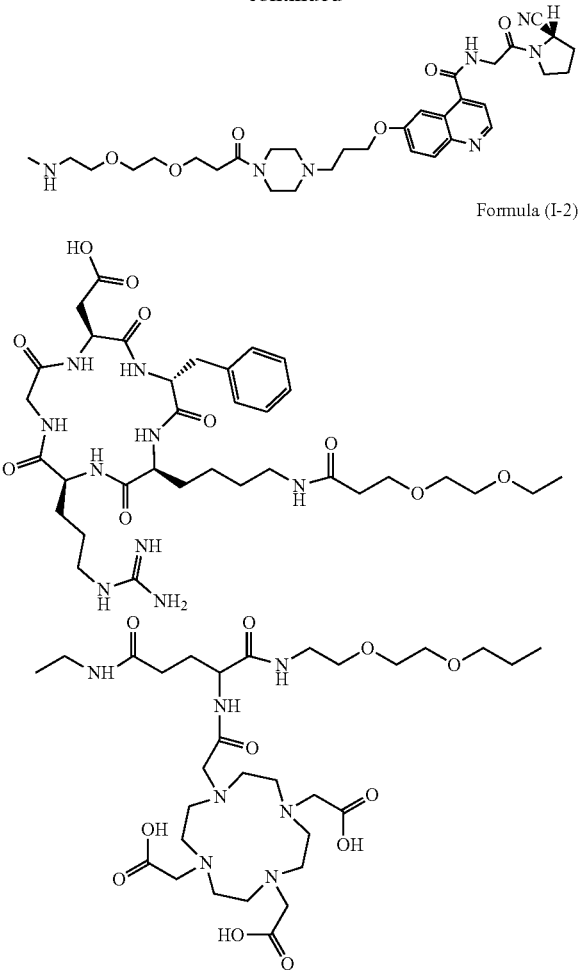

14 Claims, 13 Drawing Sheets

(51) Int. Cl.
A61K 51/04 (2006.01)
A61M 36/14 (2006.01)

(56) References Cited

FOREIGN PATENT DOCUMENTS

| CN | 113880810 A | 1/2022 |
| CN | 115286697 A | 11/2022 |
| WO | 2021168567 A1 | 9/2021 |
| WO | 2021207449 A1 | 10/2021 |
| WO | 2022040607 A1 | 2/2022 |

OTHER PUBLICATIONS

Notification to Grant issued in Chinese Application No. 2022112010812, dated Nov. 24, 2022, with English translation (2 pages).
Office Action issued in Chinese Application No. 2022112010812, dated Nov. 11, 2022, with English translation (9 pages).

Saline (0.5 h)

Saline (1 h)

Saline (4 h)

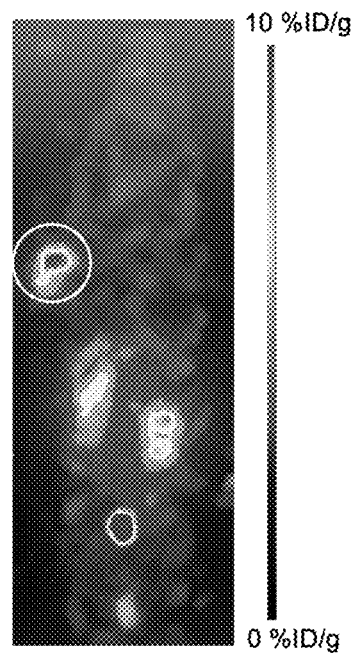
4 h
FIG. 14
FIG. 15A
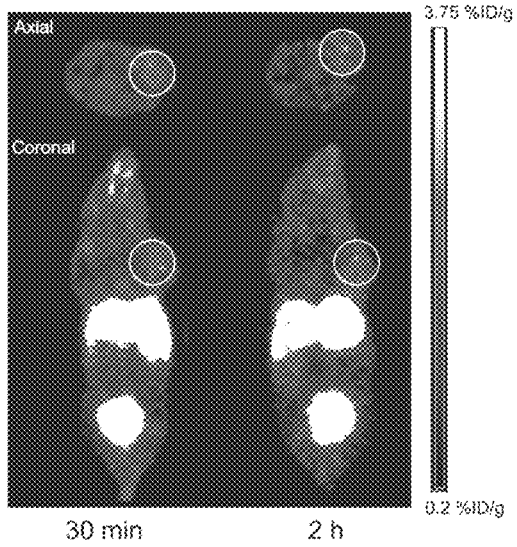
30 min    2 h
FIG. 15B
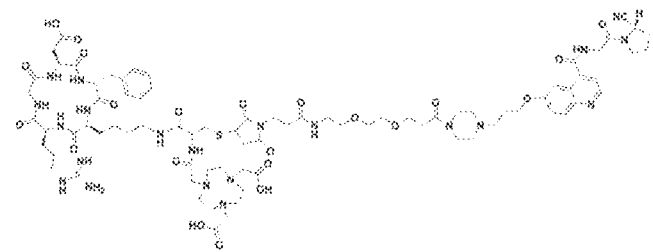
FIG. 15C
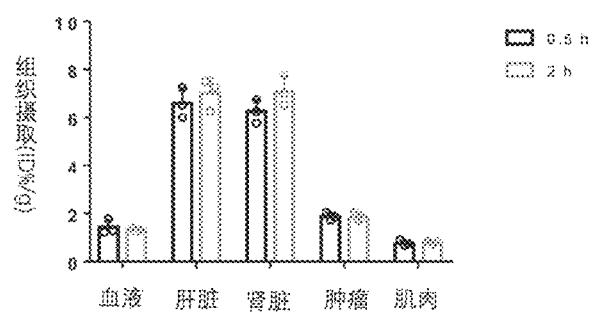

DUAL-TARGETING COMPOUND AND PREPARATION METHOD AND APPLICATION THEREOF

TECHNICAL FIELD

The present disclosure relates to the fields of nuclear medicine and molecular imaging, and specifically relates to a radionuclide labeled dual-targeting compound targeting a fibroblast activation protein (FAP) and an integrin $\alpha_v\beta_3$ and a preparation method and use of the compound in diagnosis or therapy of diseases characterized by overexpression of FAP and/or integrin αv3.

BACKGROUND

A fibroblast activation protein (FAP) is a membrane serine peptidase that is expressed on the surface of a tumor stroma activated fibroblast and plays an important role in generation and development processes of tumors. Previous studies show that the FAP is generally not expressed in normal human tissues, but selectively highly expressed on surfaces of stromal fibroblasts of more than 90% of epithelial malignant tumors, including breast cancer, ovarian cancer, lung cancer, colorectal cancer, gastric cancer and pancreatic cancer. An integrin $\alpha_v\beta_3$ is a heterodimer receptor located on surfaces of cells, which is rarely expressed in endothelial and epithelial cells of normal blood vessels, but is highly expressed on surfaces of a variety of solid tumor cells such as lung cancer, osteosarcoma, neuroblastoma, breast cancer, prostate cancer, bladder cancer, glioblastoma and invasive melanoma. Moreover, the integrin $\alpha_v\beta_3$ is highly expressed in endothelial cell membranes of new blood vessels in all tumor tissues, indicating that the integrin $\alpha_v\beta_3$ plays a key role in growth, invasion and metastasis of tumors. A polypeptide containing an arginine-glycine-aspartic acid (RGD) sequence can specifically bind to the integrin $\alpha_v\beta_3$. In view of widespread expression and important role of the FAP and the integrin $\alpha_v\beta_3$ in tumors, the FAP and the integrin $\alpha_v\beta_3$ have become important targets for imaging and therapy of tumors.

In order to further improve the diagnosis and therapy efficiency of tumors, dual-targeting probes having affinity for the two targets have already been developed in the prior art. For example, a dual-targeting probe having affinity for both a prostate specific membrane antigen (PSMA) and a gastrin releasing peptide receptor (GRPR) was reported by Anna Orlova et al. Due to high expression of the PSMA and GRPR in the prostate gland, the dual-targeting probe has the disadvantage that it can only be applied to radiodiagnosis and therapy of prostate cancer, and cannot be applied to other tumors.

SUMMARY

Due to main distribution in tumor stromal cells and new blood vessels, FAP and integrin $\alpha_v\beta_3$ are highly expressed in a variety of tumor types at the same time, and are ideal targets for development of a dual-targeting probe for "extensive tumors". Considering the heterogeneity of tumors, in order to further improve the diagnosis and therapy efficiency of tumors, a targeting compound capable of targeting the two targets FAP and integrin $\alpha_v\beta_3$ is required to be developed. The dual-targeting compound requires high affinity for the two targets at the same time to realize synergistic targeting of the FAP target and the integrin $\alpha_v\beta_3$ target in tumors, as well as excellent pharmacokinetic properties in the body to increase the uptake in tumors and prolong the retention time in tumors. A radionuclide labeled dual-targeting compound based on the dual-targeting compound can utilize the FAP target and the integrin $\alpha_v\beta_3$ target at the same time to increase the number of effective receptors in tumors and improve the utilization efficiency, so that the problem of improving the detection efficiency and/or therapy efficiency of positive tumors is solved.

In order to solve the above problems, a primary purpose of the present disclosure is to develop a novel compound structure capable of realizing synergistic targeting of the FAP target and the integrin $\alpha_v\beta_3$ target in tumors to improve the uptake of a medicine in tumors and prolong the retention time.

Another purpose of the present disclosure is to provide a method for preparing the novel compound. The compound capable of realizing synergistic targeting of the FAP target and the integrin $\alpha_v\beta_3$ target in tumors is synthesized by a convenient and αvailable synthetic route.

Another purpose of the present disclosure is to provide application of the compound in diagnosis or therapy of diseases characterized by overexpression of FAP and/or integrin $\alpha_v\beta_3$.

The above purposes of the present disclosure are realized by adopting the following technical solutions.

In the first aspect, the present disclosure provides a dual-targeting compound capable of targeting FAP and integrin $\alpha_v\beta_3$. The compound structurally contains ligand structures specifically binding to FAP and integrin $\alpha_v\beta_3$ at the same time, and the compound has the following structure shown in Formula (I):

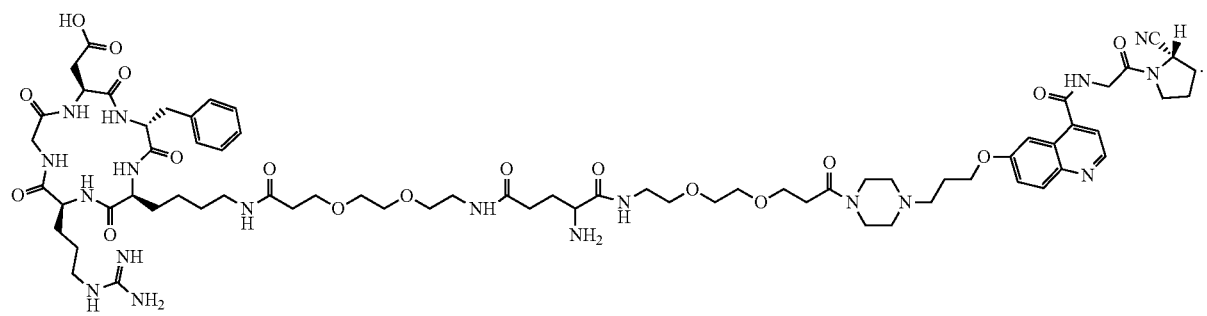

In the second aspect, the present disclosure also provides a dual-targeting compound capable of being labeled with a radionuclide for targeting FAP and integrin $\alpha_v\beta_3$. The compound structurally contains ligand structures specifically binding to FAP and integrin $\alpha_v\beta_3$ at the same time and a nuclide chelating structure. The structure of the compound is denoted as an FAPI-RGD structure in the present disclosure, and the compound has the following structure shown in Formula (I-1) or Formula (1-2):

Formula (I-1)

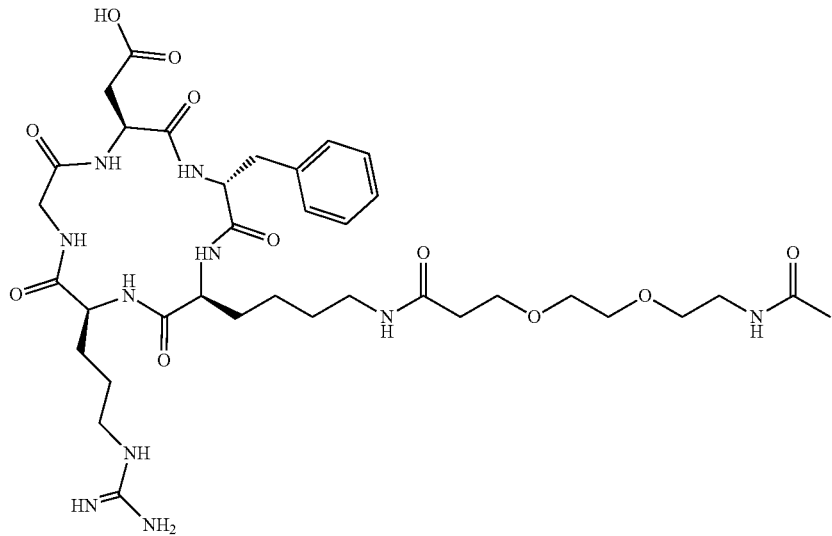

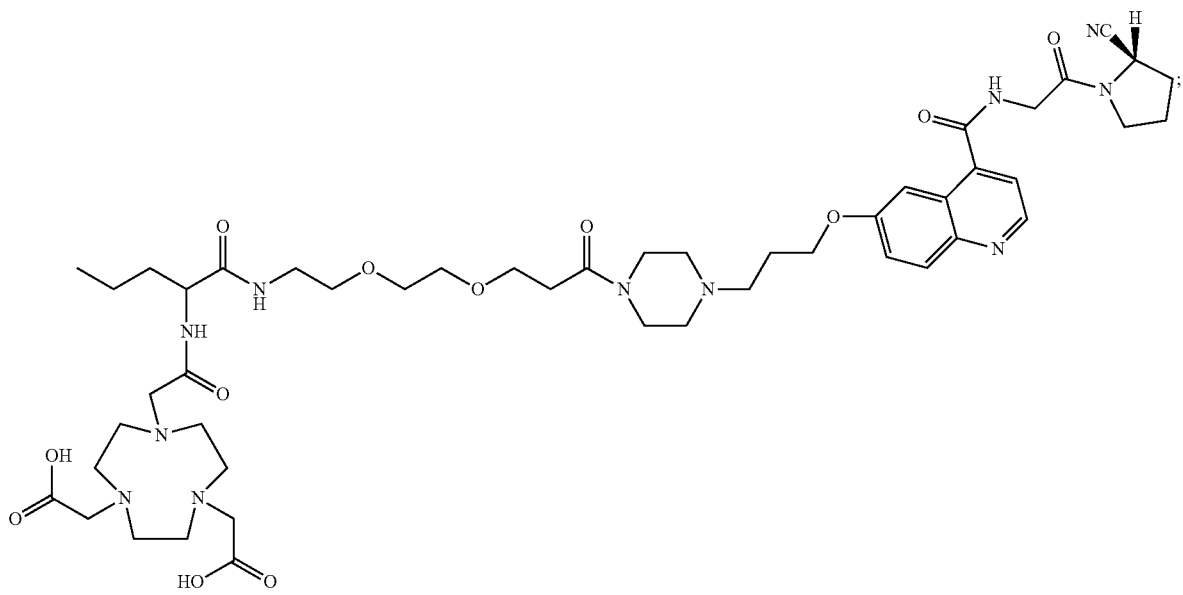

Formula (I-2)

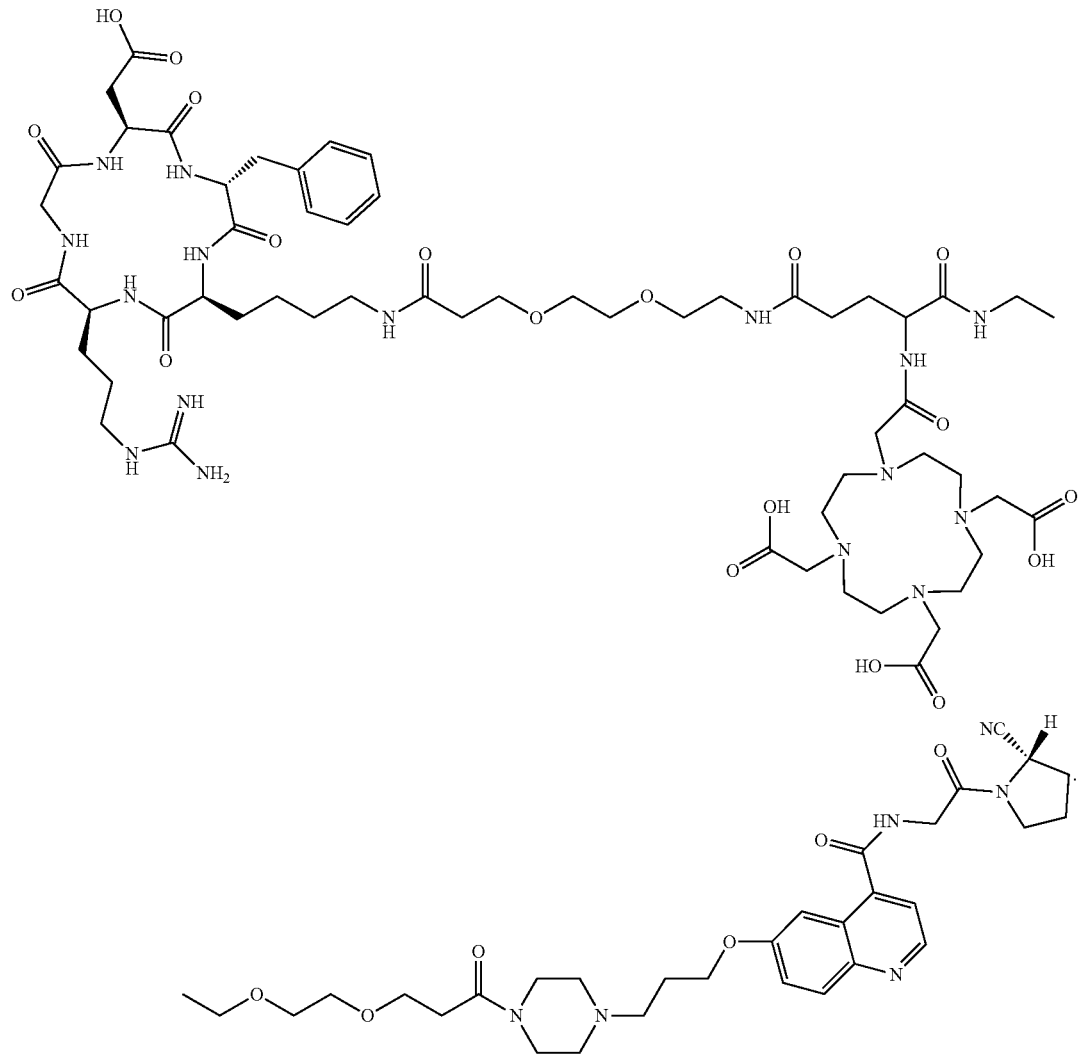

In the third aspect, the present disclosure provides a radionuclide labeled dual-targeting compound capable of targeting FAP and integrin $α_vβ_3$. The compound is obtained by labeling the compound as described in the second aspect of the present disclosure with a radionuclide.

In the solution of the present disclosure, the radionuclide may be selected from an α-ray emitting isotope, a β-ray emitting isotope, a γ-ray emitting isotope, an auger electron emitting isotope, or an X-ray emitting isotope, such as any one of $^{18}$F, $^{51}$Cr, $^{67}$Ga, $^{68}$Ga, $^{111}$In, $^{99m}$Tc, $^{186}$Re, $^{188}$Re, $^{139}$La, $^{140}$La, $^{175}$Yb, $^{153}$Sm, $^{166}$Ho, $^{86}$Y, $^{90}$Y, $^{149}$Pm, $^{165}$Dy, $^{169}$Er, $^{177}$Lu, $^{47}$Sc, $^{142}$Pr, $^{159}$Gd, $^{212}$Bi, $^{213}$Bi, $^{72}$As, $^{72}$Se, $^{97}$Ru, $^{109}$Pd, $^{105}$Rh, $^{105}$Rh, $^{101m}$Rh, $^{119}$Sb, $^{128}$Ba, $^{123}$I, $^{124}$I, $^{131}$I, $^{197}$Hg, $^{159}$Gd, $^{212}$Bi, $^{213}$Bi, $^{72}$As, $^{72}$Se, $^{97}$Ru, $^{109}$Pd, $^{105}$Rh, $^{101m}$Rh, $^{119}$Sb, $^{128}$Ba, $^{123}$I, $^{124}$I, $^{131}$I, $^{197}$Hg, $^{211}$At, $^{151}$Eu, $^{153}$Eu, $^{169}$Eu, $^{201}$Tl, $^{203}$Pb, $^{212}$Pb, $^{64}$Cu, $^{67}$Cu, $^{198}$Au, $^{225}$Ac, $^{227}$Th, $^{89}$Zr, or $^{199}$Ag; and the radionuclide is more preferably $^{18}$F, $^{64}$Cu, $^{68}$Ga, $^{89}$Zr, $^{90}$Y $^{111}$In, $^{99m}$Tc, $^{177}$Lu, $^{188}$Re, or $^{225}$Ac.

In the fourth aspect, the present disclosure provides a method for preparing the dual-targeting compound as described in the second aspect and a radionuclide labeled compound thereof (namely the dual-targeting compound as described in the third aspect of the present disclosure). The preparation method provided by the present disclosure includes:

(1) reacting 6-hydroxyquinoline-4-carboxylic acid with amino of tert-butyl glycinate first by condensation; then connecting Boc-protected piperazinyl at hydroxyl position of an amide condensation product by an alkyl chain; removing Boc protective groups and tert-butyl protective groups under acidic conditions, and introducing a Boc protective group to piperazine ring of the condensation product, followed by an amide condensation reaction with (S)-pyrrolidene-2-carbonitrile hydrochloride; after removing the Boc protective group, carrying out a condensation reaction with N-Boc-3-[2-(2-aminoethoxy)ethoxy]propionic acid; next, removing the Boc protective group, and carrying out a reaction with Fmoc-O-tert-butyl-L-glutamic acid; after removing tert-butyl ester, preparing an activated ester, followed by a reaction with c(RGDfK) with amino-dipolyethylene glycol to obtain a dual-targeting compound; then after removing an Fmoc protective group, carrying out a reaction with a nuclide chelating agent, where the nuclide chelating agent is 1,4,7,10- tetraazacyclododecane-N,N',N,N'-tetraacetic acid or 1,4,7-triazacyclononane-1,4,7-triacetic acid; and finally, removing a tert-butyl protective group on a chelating group to obtain a dual-targeting compound capable of being labeled with a radionuclide, namely the dual-targeting compound as described in the second aspect of the present disclosure; and (2) reacting the dual-targeting compound capable of being labeled with a radionuclide obtained in step (1) with compound containing a radionuclide by a prior art of wet labeling or freeze-drying labeling to obtain the radionuclide labeled dual-targeting compound capable of targeting FAP and integrin $\alpha_v\beta_3$ as described in the third aspect of the present disclosure.

In the fifth aspect, the present disclosure provides a pharmaceutical composition. The pharmaceutical composition includes the dual-targeting compound capable of targeting FAP and integrin $\alpha_v\beta_3$ as described in the first aspect of the present disclosure, the dual-targeting compound capable of being labeled with a radionuclide for targeting FAP and integrin $\alpha_v\beta_3$ as described in the second aspect of the present disclosure, the radionuclide labeled dual-targeting compound capable of targeting FAP and integrin $\alpha_v\beta_3$ as described in the third aspect, or any pharmaceutically acceptable tautomer, racemate, hydrate, solvate or salt thereof.

In the sixth aspect, the present disclosure also provides application of the dual-targeting compound capable of targeting FAP and integrin $\alpha_v\beta_3$ as described in the first aspect of the present disclosure, the dual-targeting compound capable of being labeled with a radionuclide for targeting FAP and integrin $\alpha_v\beta_3$ as described in the second aspect, the radionuclide labeled dual-targeting compound capable of targeting FAP and integrin $\alpha_v\beta_3$ as described in the third aspect, or the pharmaceutical composition as described in the fifth aspect in preparation of medicines for diagnosis or therapy of diseases characterized by overexpression of FAP and/or integrin $\alpha_v\beta_3$ in animals or human persons.

In the application of the present disclosure, the diseases characterized by overexpression of FAP and/or integrin $\alpha_v\beta_3$ include, but are not limited to: cancer, chronic inflammation, atherosclerosis, fibrosis, tissue remodeling and cicatricial diseases; and preferably, the cancer is further selected from breast cancer, pancreatic cancer, small bowel cancer, colon cancer, rectal cancer, lung cancer, head and neck cancer, ovarian cancer, hepatocellular carcinoma, esophageal cancer, hypopharyngeal cancer, nasopharyngeal cancer, laryngeal cancer, myeloma cells, bladder cancer, cholangiocellular carcinoma, clear cell renal cell carcinoma, neuroendocrine carcinoma, carcinogenic osteomalacia, sarcoma, CUP (cancer of unknown primary), thymic carcinoma, glioma, neuroglioma, astrocytoma, cervical cancer, or prostate cancer.

The structure of the FAPI-RGD compound provided by the present disclosure has high affinity for the FAP target and the integrin $\alpha_v\beta_3$ target, can realize synergistic targeting of the FAP target and the integrin $\alpha_v\beta_3$ target in tumors, exhibits high uptake in tumors and long retention time in tumors, and is expected to be applied to diagnosis or therapy of diseases characterized by overexpression of FAP and/or integrin αv03.

In addition, the preparation method of the FAPI-RGD compound provided by the present disclosure has simple reaction route, simple operation, cheap and readily available raw materials and low production cost, and is suitable for industrial production.

BRIEF DESCRIPTION OF DRAWINGS

FIG. 14 is a diagram showing SPECT imaging results of $^{177}$Lu-FAPI-RGD complex prepared in Example 4 of the present disclosure in HT1080-FAP tumor-bearing mice.

FIGS. 15A-15C are diagrams showing the molecular structure of a complex of $^{68}$GA labeled control compound FAPI-RGD, MicroPET imaging results 30 min and 2 h after the control compound is injected into HT1080-FAP tumor-bearing mice, and statistics of uptake results in tumors and vital organs.

DETAILED DESCRIPTION OF EMBODIMENTS

Figure 1:
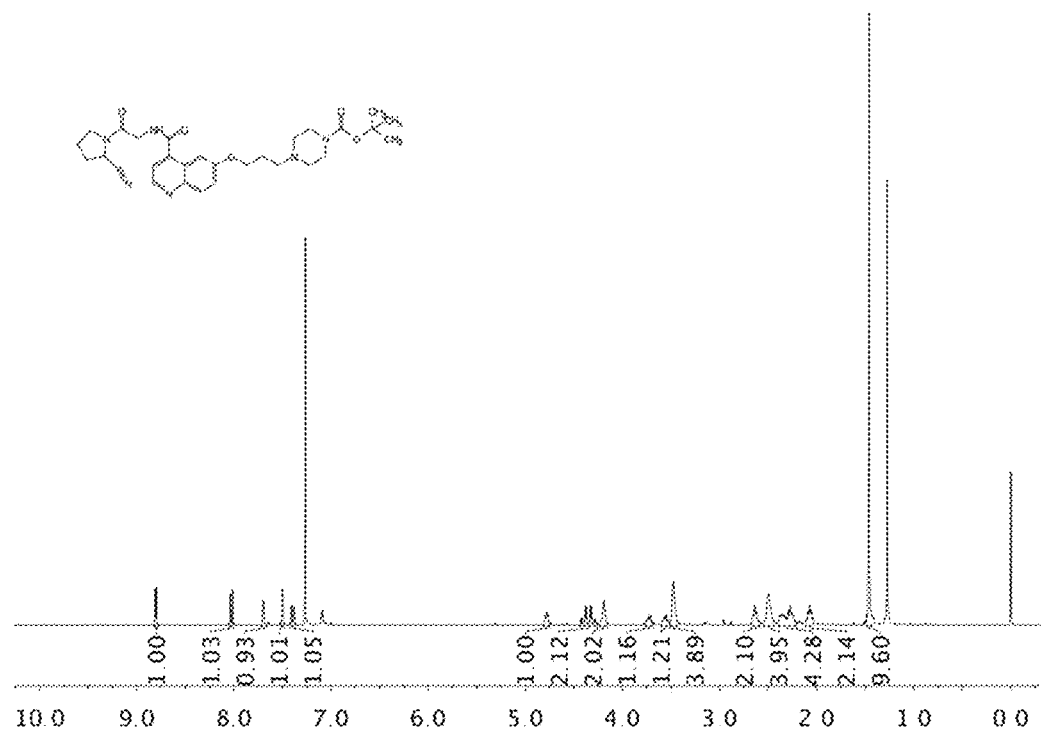
FIG. 1 is a diagram showing nuclear magnetic hydrogen spectrum of compound 7.

Technical solutions of the present disclosure are further explained and described below in conjunction with specific embodiments and attached drawings.

Example 1: Preparation of Compound (I-1)

Synthesis of Compound 2

Compound 1 (6-hydroxyquinoline-4-carboxylic acid, 1.89 g, 10.0 mmol), tert-butyl glycinate (1.89 g, 10.0 mmol), HATU (3.8 g, 10.0 mmol) and N,N-diisopropylethylamine (2.6 g, 20.0 mmol) were sequentially put into 30 mL of N,N-dimethylformamide in a 100 mL flask. A reaction mixture was stirred overnight, and reduced pressure distillation was conducted to remove the solvent to obtain a crude product. Then purification was conducted with a silica gel column (ratio of dichloromethane to methanol was 30:1) to obtain white solid compound 2 with a yield of 87%.

Synthesis of Compound 3

Compound 2 (1.51 g, 5.0 mmol), 1-bromo-3-chloropropane (1.55 g, 10.0 mmol) and potassium carbonate (1.38 g, 10.0 mmol) were sequentially put into 50 mL of N,N-dimethylformamide in a 100 mL flask. The system was heated to 60° C. and stirred overnight at 60° C., and reduced pressure distillation was conducted to remove the solvent to obtain a crude product. Then purification was conducted with a silica gel column (ratio of dichloromethane to methanol was 50:1) to obtain white solid compound 3 with a yield of 63%.

Synthesis of Compound 4

Compound 3 (0.76 g, 2.0 mmol), tert-butyl 1-piperazinecarboxylate (0.55 g, 3.0 mmol) and potassium iodide (0.49 g, 3.0 mmol) were sequentially put into 30 mL of acetonitrile in a 100 mL flask. The system was heated to 60° C. and stirred overnight at 60° C., and reduced pressure distillation was conducted to remove the solvent to obtain a crude product. Then purification was conducted with a silica gel column (ratio of dichloromethane to methanol was 30:1) to obtain white solid compound 4 with a yield of 58%.

Synthesis of Compound 5

Compound 4 (0.52 g, 1.0 mmol) was dissolved in 10 mL of a mixed solution of dichloromethane and trifluoroacetic acid (at a volume ratio of 9:1) in an ice bath. The system was heated to room temperature for reaction for 2 h, and after the reaction was completed, reduced pressure distillation was conducted to remove the solvent. Then resulting product was dissolved in 10 mL of N,N-dimethylformamide to obtain compound 5 for later use.

Synthesis of Compound 6

Di-tert-butyl dicarbonate (0.22 g, 1.0 mmol) and N,N-diisopropylethylamine (0.39 g, 3.0 mmol) were separately added to an N,N-dimethylformamide solution of compound 5. The system was stirred overnight at room temperature, and reduced pressure distillation was conducted to remove the solvent to obtain a crude product. Then purification was conducted with a silica gel column (ratio of dichloromethane to methanol was 10:1) to obtain white solid compound 6 with a yield of 72%.

Synthesis of Compound 7

Figure 2:
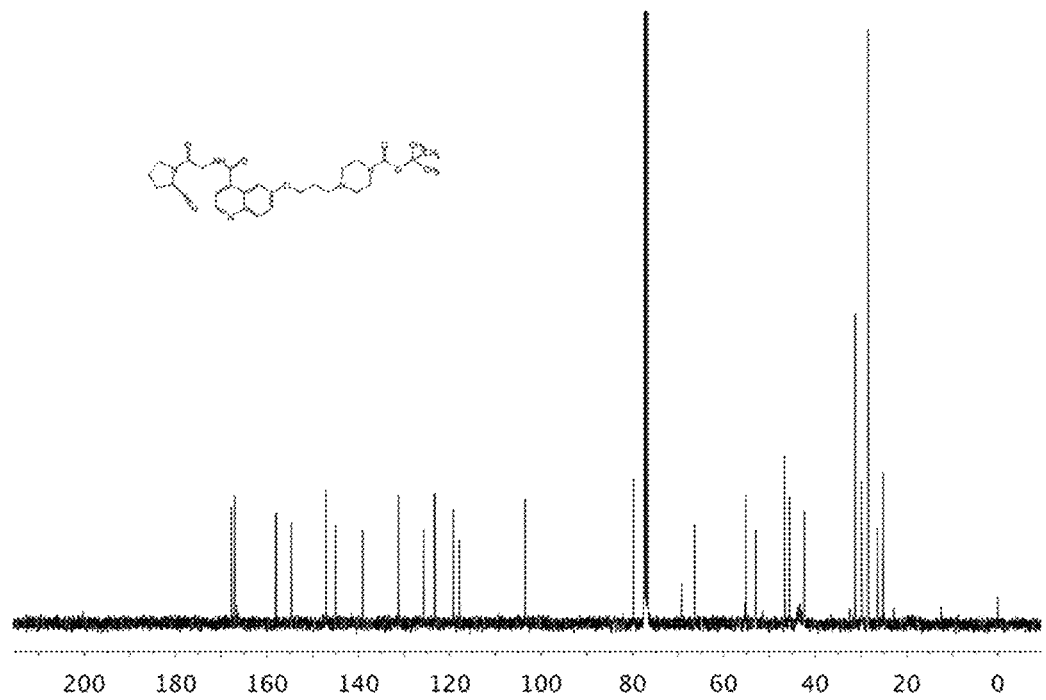
FIG. 2 is a diagram showing nuclear magnetic carbon spectrum of compound 7.
Figure 3:
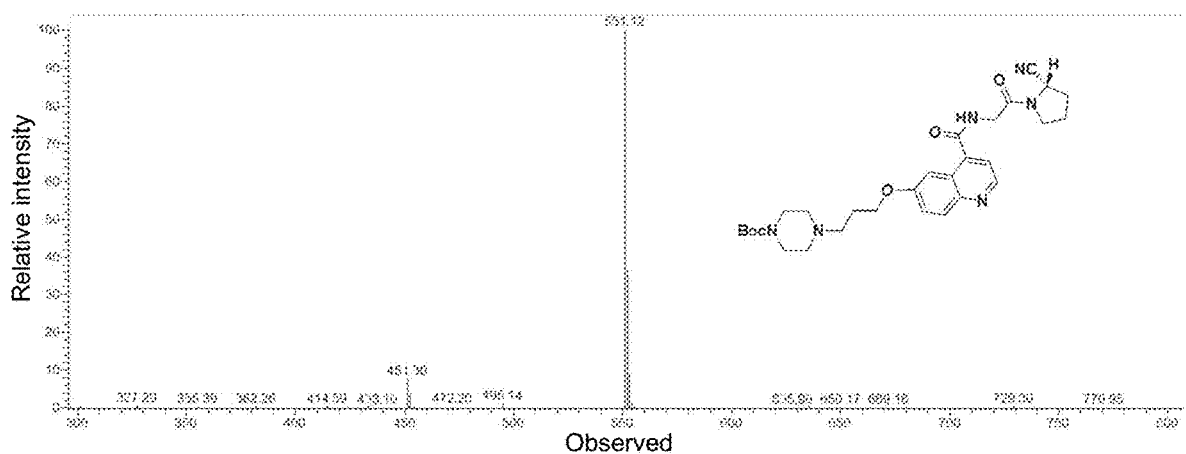
FIG. 3 is a diagram showing mass spectrum of compound 7.

Compound 6 (0.47 g, 1.0 mmol), (S)-pyrrolidene-2-carbonitrile hydrochloride (0.13 g, 1.0 mmol), HATU (0.38 g, 1.0 mmol) and N,N-diisopropylethylamine (0.26 g, 2.0 mmol) were sequentially put into 10 mL of N,N-dimethylformamide in 100 mL flask. A reaction mixture was stirred at room temperature until a reaction was completed, and reduced pressure distillation was conducted to remove the solvent to obtain a crude product. Then purification was conducted with a silica gel column (ratio of dichloromethane to methanol was 50:1) to obtain white solid compound 7 with a yield of 85%. FIG. 1 shows the magnetic hydrogen spectrum of compound 7. FIG. 2 shows the nuclear magnetic carbon spectrum of compound 7. FIG. 3 is a diagram showing the mass spectrum of compound 7.

Synthesis of Compound 8

Figure 4:
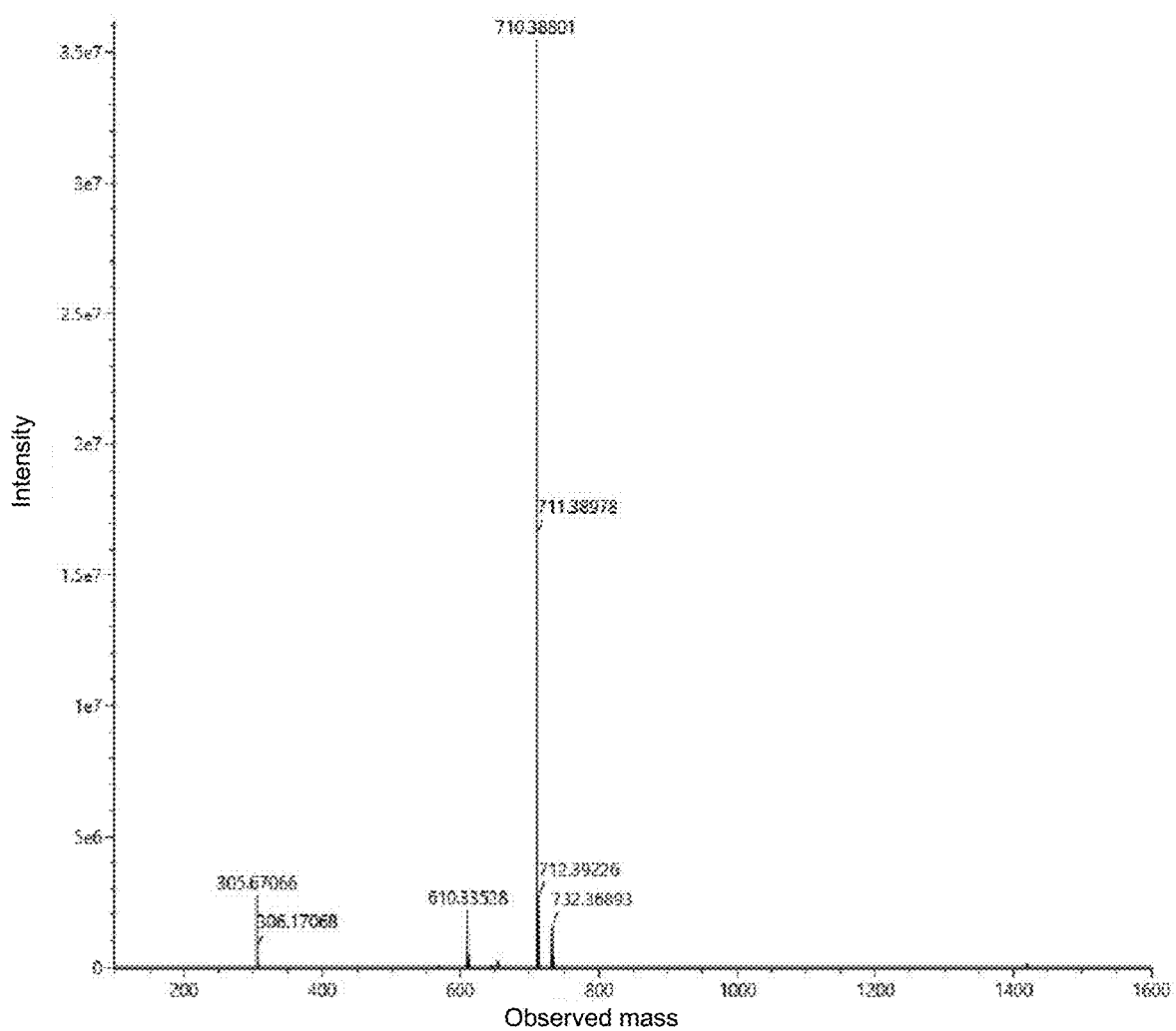
FIG. 4 is a diagram showing mass spectrum of compound 8.

Compound 7 (2.50 g, 4.5 mmol), p-toluenesulfonic acid monohydrate (2.58 g, 13.6 mmol) and 25 mL of acetonitrile were added to a reaction flask for a reaction at 65° C. for 1 h. After monitoring by TLC (ratio of methanol to dichloromethane was 5:1) that compound 7 was completely reacted, evaporation to dryness was conducted under reduced pressure at 40° C. 14 ml of DMF and DIPEA (3.05 g, 23.6 mmol) were added and stirred at 25° C. for a reaction (1), during which a protective group was removed from piperazinyl of compound 7, to obtain an intermediate. N-tert-butoxycarbonyl-dipolyethylene glycol-carboxylic acid (1.62 g, 4.8 mmol), HATU (2.60 g, 6.8 mmol) and 10 mL of DMF were added to another reaction flask for a reaction (2) at 25° C. for 30 min. A reaction solution system obtained after the reaction (2) was added dropwise to a reaction system (1) for a reaction for 1 h. Evaporation to dryness was conducted under reduced pressure at 40° C. 50 mL of purified water was added, and extraction was conducted for two times with 50 mL of DCM each time. The DCM was combined, and drying was conducted with anhydrous sodium sulfate, followed by filtration and evaporation to dryness to obtain a crude product. The crude product was purified by column chromatography to obtain 1.68 g of a target compound. The theoretical molecular weight was 709.3799, the measured molecular weight was 709.38801, and the mass spectrum results were consistent with that of the target compound. FIG. 4 is a diagram showing the mass spectrum of compound 8.

Synthesis of Compound 9

Figure 5:
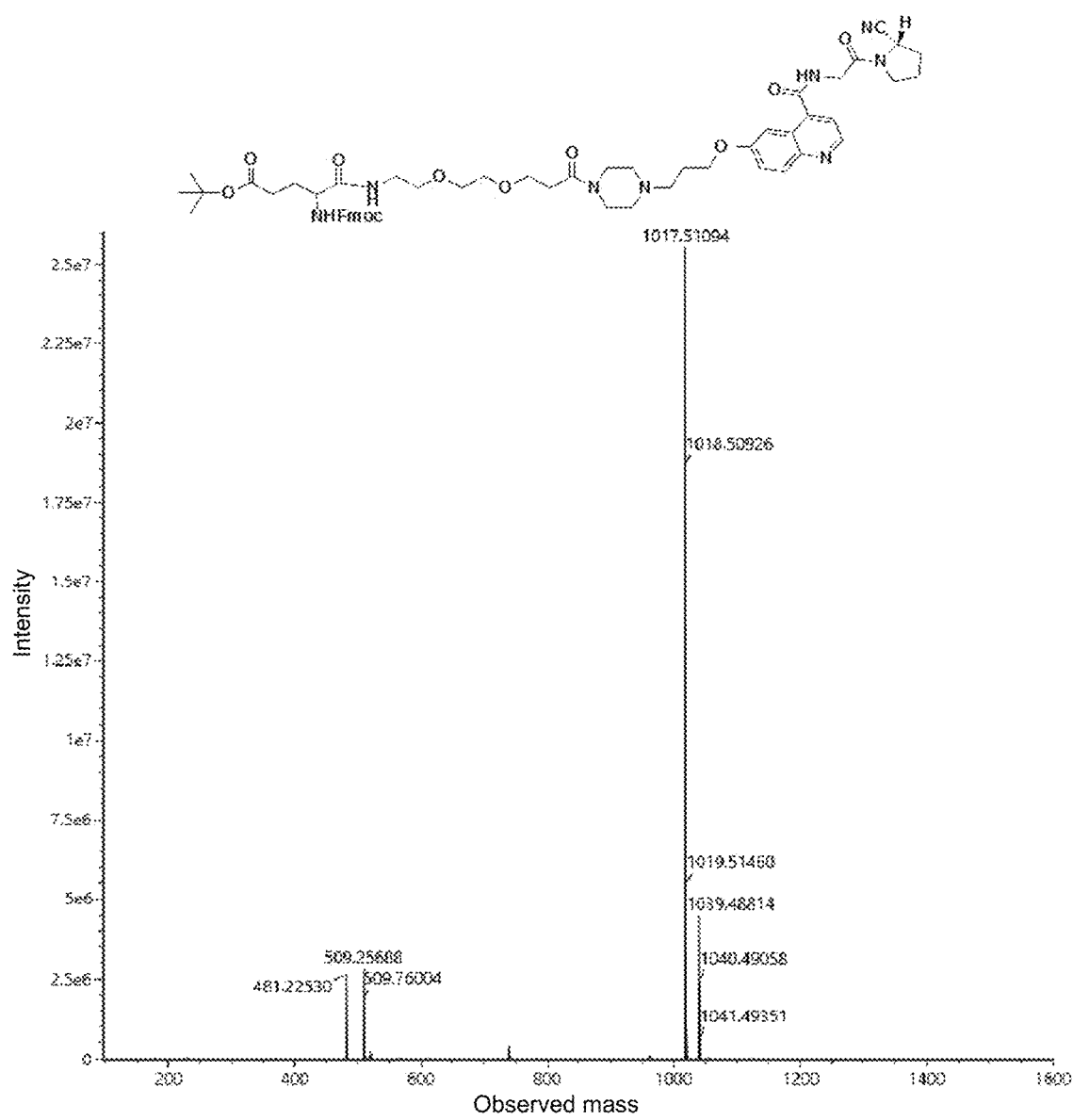
FIG. 5 is a diagram showing mass spectrum of compound 9.

Compound 8, p-toluenesulfonic acid monohydrate (1.61 g, 8.5 mmol) and 20 mL of acetonitrile were added to a reaction flask for a reaction at 65° C. for 1 h, and evaporation to dryness was conducted under reduced pressure at 40° C. 20 ml of DMF and DIPEA (1.83 g, 14.2 mmol) were added and stirred for a reaction (1) at 25° C. Fmoc-o-tert-butyl-L-glutamic acid (1.43 g, 3.4 mmol), HATU (1.29 g, 3.4 mmol) and 20 mL of DMF were added to another reaction flask for a reaction (2) at 25° C. for 30 min. A reaction solution system obtained after the reaction (2) was added dropwise to a reaction system (1) for a reaction for 1 h. Evaporation to dryness was conducted under reduced pressure at 40° C. to obtain a crude product, and the crude product was purified by column chromatography to obtain 1.19 g of target compound. The theoretical molecular weight was 1016.5008, the measured molecular weight was 1016.51094, and the mass spectrum results were consistent with that of the target compound. FIG. 5 is a diagram showing the mass spectrum of compound 9.

Figure 6:
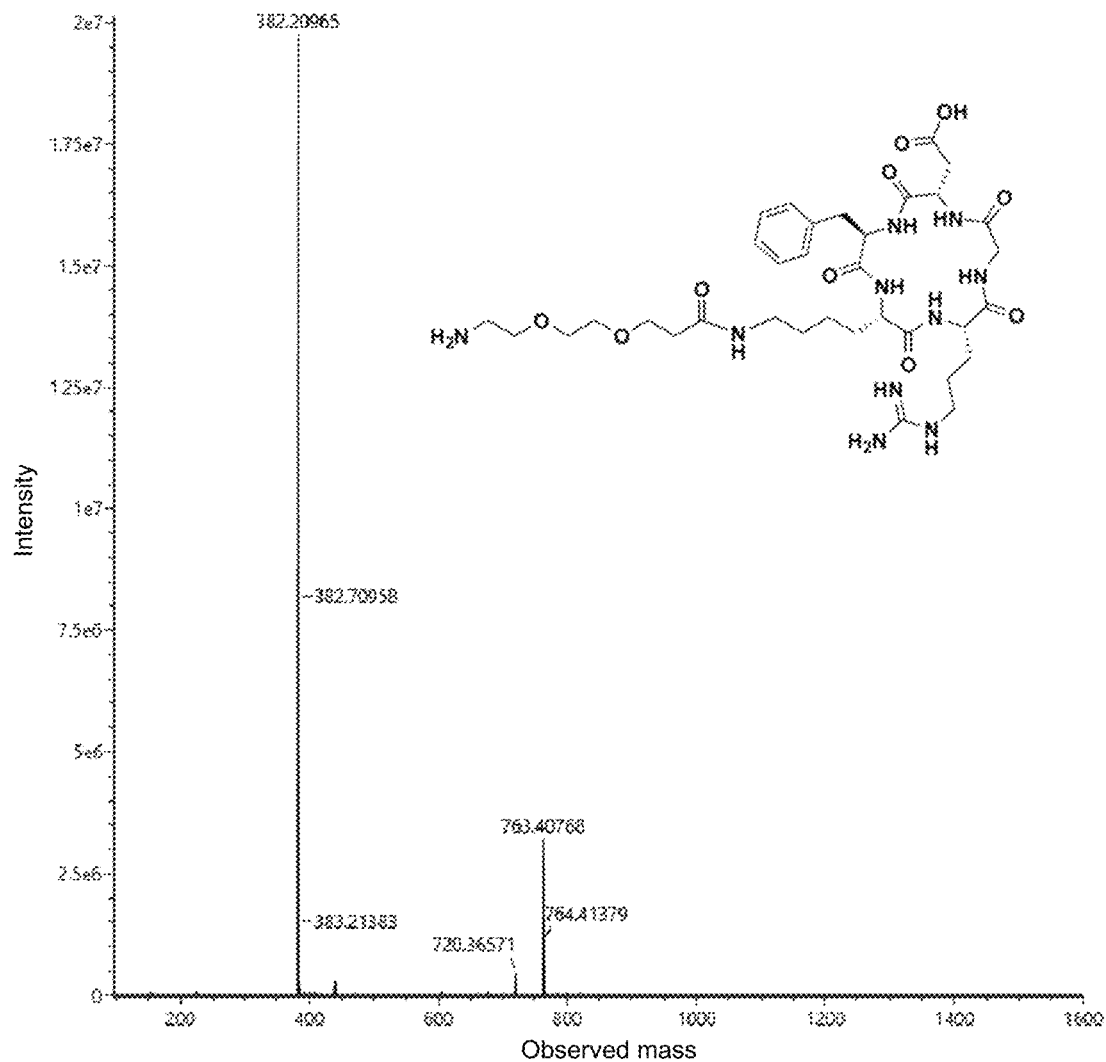
FIG. 6 is a diagram showing mass spectrum of compound 12.

Synthesis of Compound 12 c(RGDfK) (1.00 g, 1.7 mmol), tert-butyl amino-dipolyethylene glycol-succinimide (0.74 g, 1.9 mmol), DIPEA (0.44 g, 3.4 mmol) and 20 mL of DMF were added to a reaction flask for a reaction at 30° C. for 20 h. Evaporation to dryness was conducted under reduced pressure at 40° C., 10 mL of methanol was added, and 60 mL of MTBE was added dropwsie for precipitating solid to obtain an intermediate 11. Next, suction filtration was conducted, followed by vacuum drying at 40° C. for 2 h. The solid intermediate 11 was added to the reaction flask, and 30 mL of TFA and 1.5 mL of purified water were added for a reaction at 30° C. for 1 h, followed by cooling to 0-5° C. Then, 200 mL of MTBE was added dropwise and stirred at 0-5° C. for 30 min, followed by suction filtration, rinsing with MTBE and vacuum drying at 40° C. to obtain a product. The theoretical molecular weight was 762.4024, the measured molecular weight was 762.40768, and the mass spectrum results were consistent with that of the target compound. FIG. 6 is a diagram showing the mass spectrum of compound 12.

Synthesis of Compound 13

Figure 7:
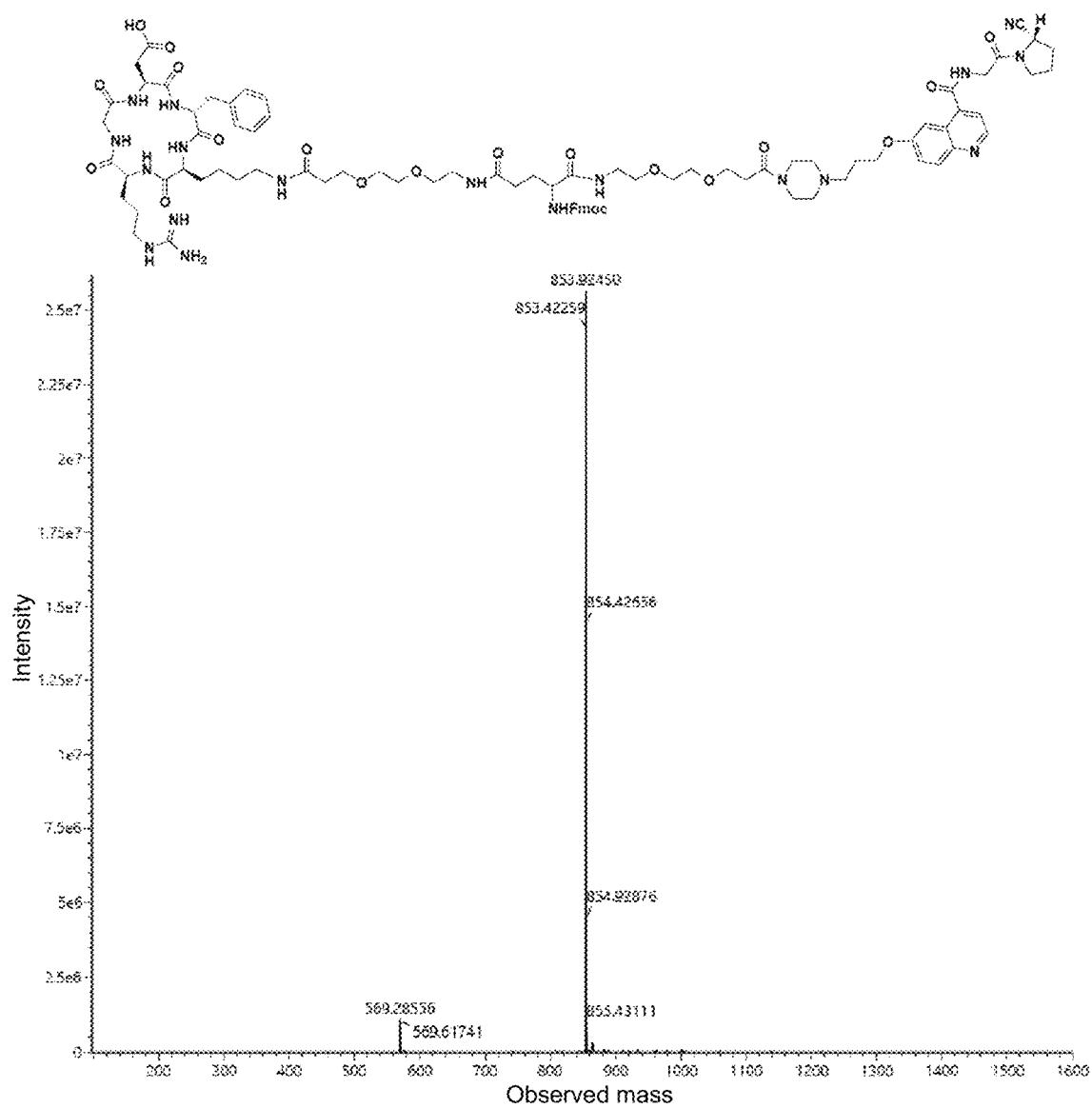
FIG. 7 is a diagram showing mass spectrum of compound 13.

Compound 9, p-toluenesulfonic acid monohydrate (0.34 g, 1.8 mmol) and 20 mL of acetonitrile were added to a reaction flask for a reaction at 65° C. for 4 h, and evaporation to dryness was conducted under reduced pressure at 40° C. 20 mL of DMF, DIPEA (0.36 g, 2.8 mmol), DCC (0.14 g, 0.7 mmol) and NHS (0.08 g, 0.7 mmol) were added for a reaction at 35° C. for 15-20 h to obtain an intermediate 10, followed by cooling to 25° C. Compound 12 was added for a reaction for 1 h, and evaporation to dryness was conducted under reduced pressure at 40° C. to obtain a crude product. The crude product was purified by a preparative liquid phase to obtain 66.5 mg of target compound. The theoretical molecular weight was 1704.8300, the measured molecular weight was 1704.84518, and the mass spectrum results were consistent with that of the target compound. FIG. 7 is a diagram showing the mass spectrum of compound 13.

Synthesis of Compound 14

Figure 8:
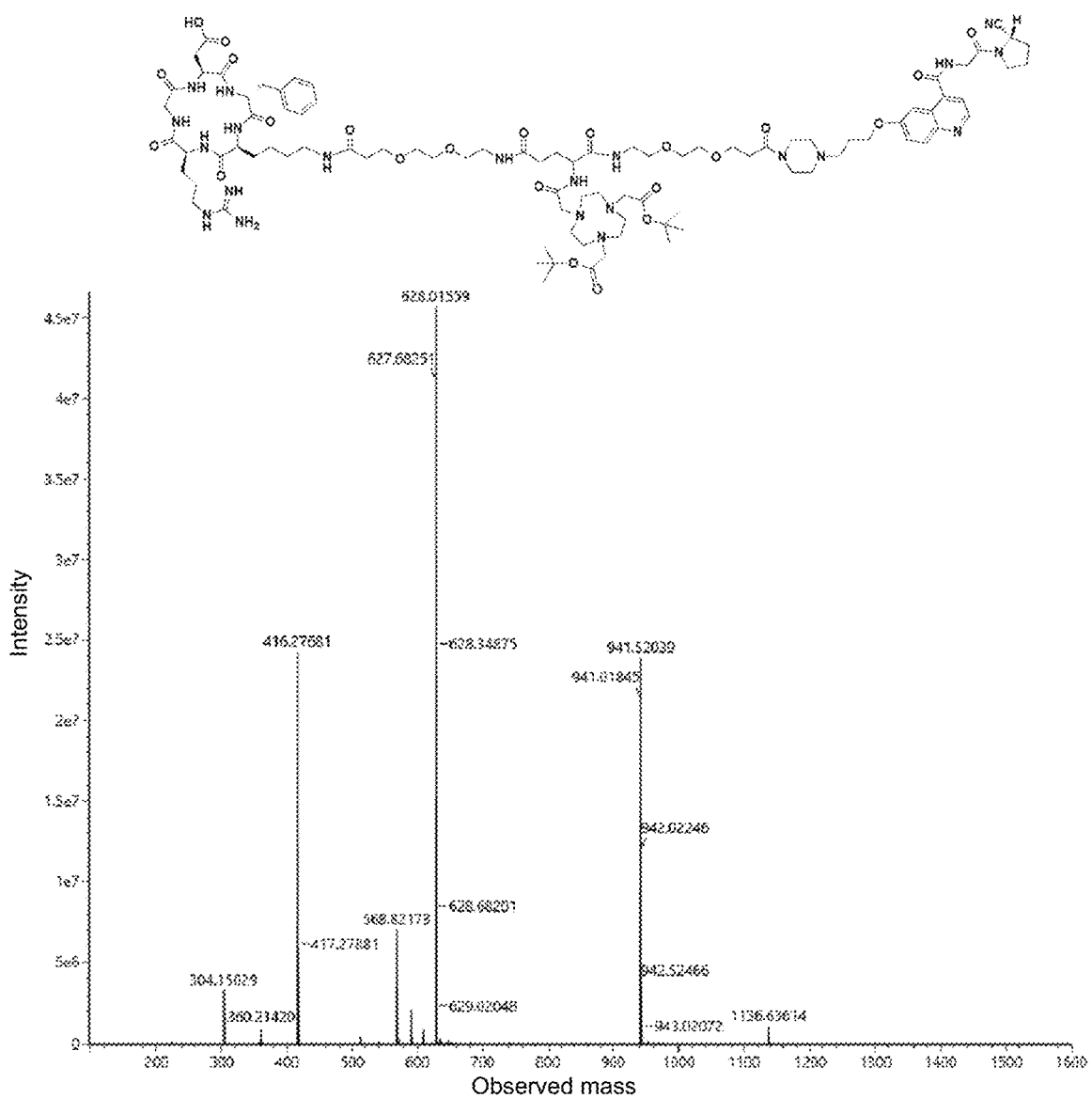
FIG. 8 is a diagram showing mass spectrum of compound 14.

Compound 13, 0.5 mL of piperidine and 2 mL of DMF were added to a reaction flask for a reaction at 25° C. for 1 h, 10 mL of ethyl acetate was added dropwise for crystallization, stirring was conducted for 30 min, followed by suction filtration to obtain a solid, and the solid was subjected to vacuum drying at 40° C. for 2 h to obtain 50.8 mg of a product. Compound 13 without an FMOc protective group was dissolved in 2 mL of DMF, NOTA-2-tert-butyl-NHS-activated ester and DIPEA (0.010 g, 0.08 mmol) were added for a reaction at 25° C. for 1 h, and evaporation to dryness was conducted under reduced pressure at 40° C. 2 mL of ethyl acetate and 2 mL of MTBE were added for crystallization, and stirring was conducted for 20 min, followed by suction filtration and vacuum drying at 40° C. to obtain 43.2 mg of product. The theoretical molecular weight was 1880.0196, the measured molecular weight was 1880.0369, and the mass spectrum results were consistent with that of the target compound. FIG. 8 is a diagram showing the mass spectrum of compound 14.

Synthesis of Compound 15

Figure 9:
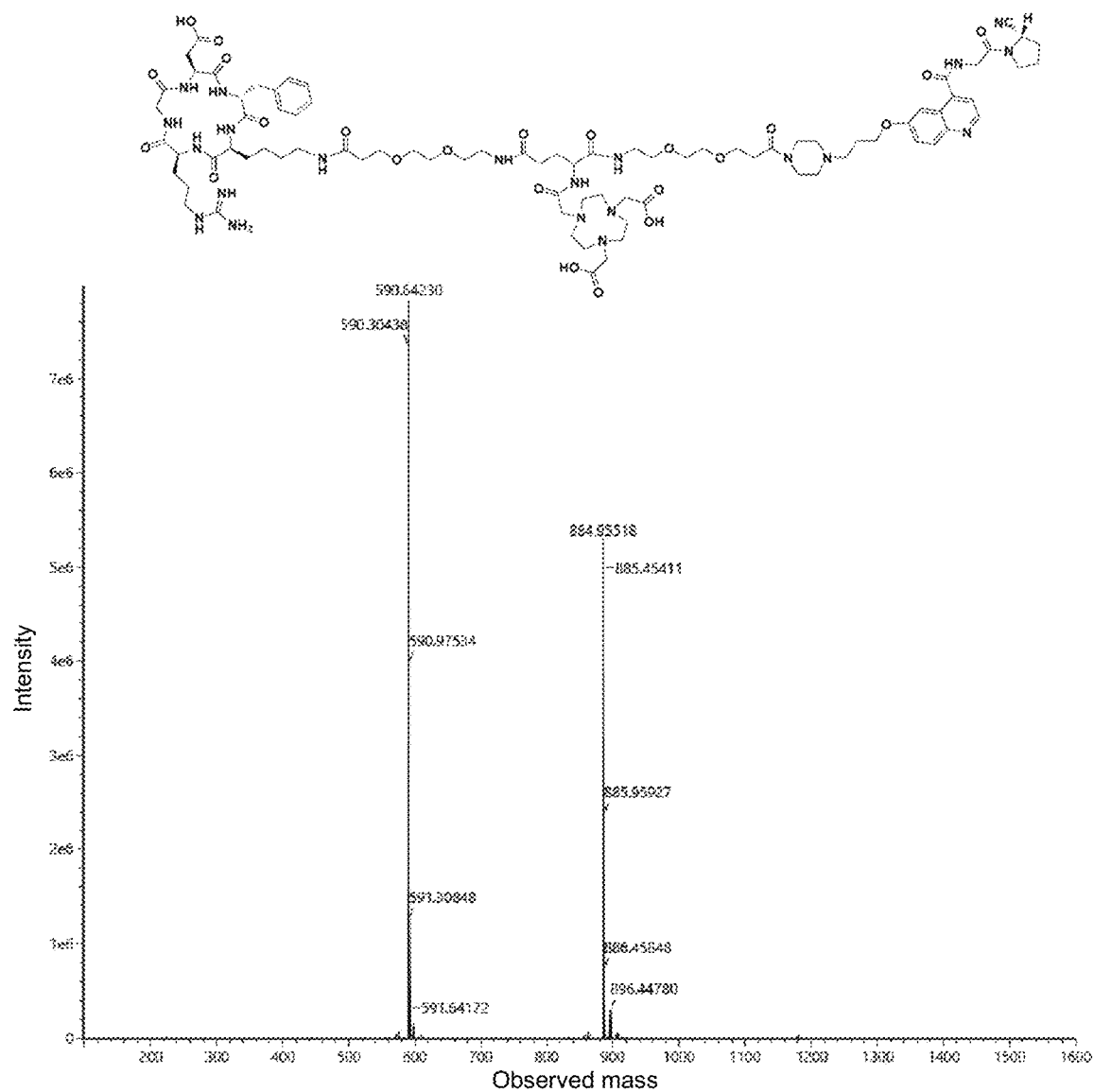
FIG. 9 is a diagram showing mass spectrum of compound 15.

Compound 14 and 2 mL of trifluoroacetic acid were added to a reaction flask for a reaction at 25° C. for 1 h, and evaporation to dryness was conducted under reduced pressure at 40° C. to obtain a crude product. The crude product was purified by a preparative liquid phase and then freeze-dried to obtain product compound 15 with a yield of 42%. The theoretical molecular weight was 1767.8944, the measured molecular weight was 1767.91036, and the mass spectrum results were consistent with that of the target compound. FIG. 9 is a diagram showing the mass spectrum of compound 15.

A synthesis route in the above steps is as follows:

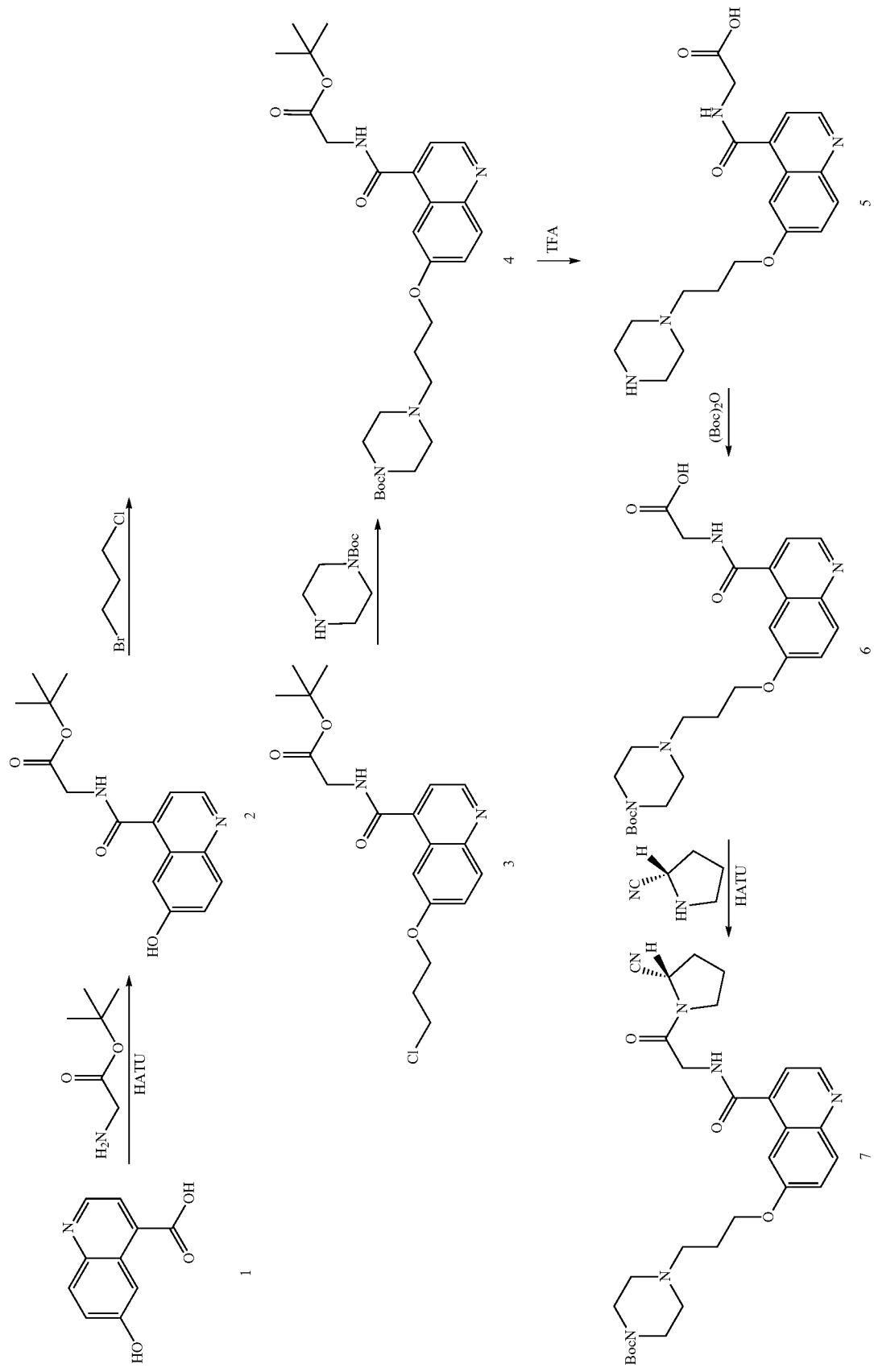

-continued
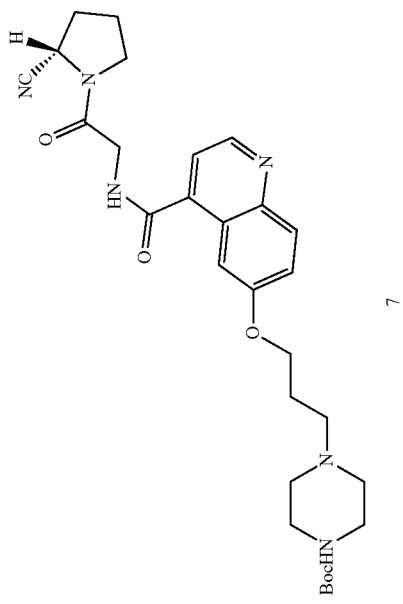
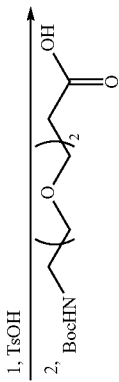
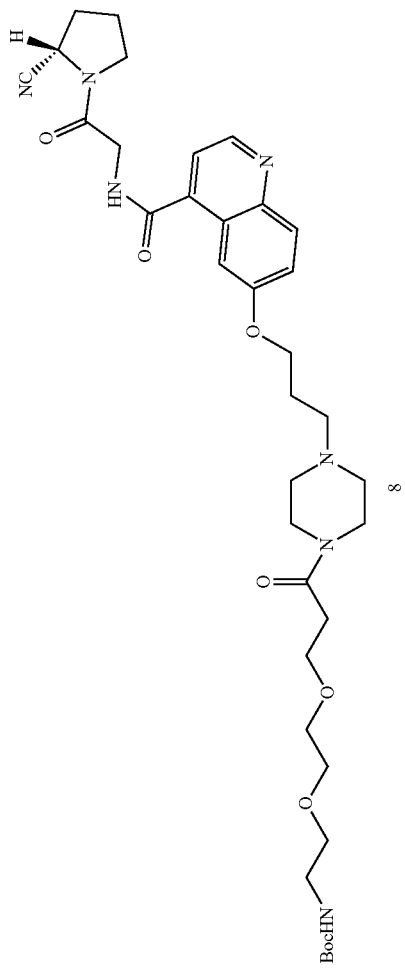
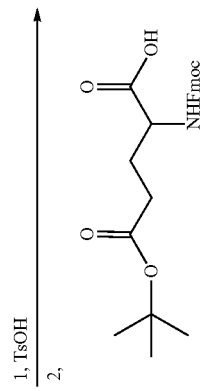

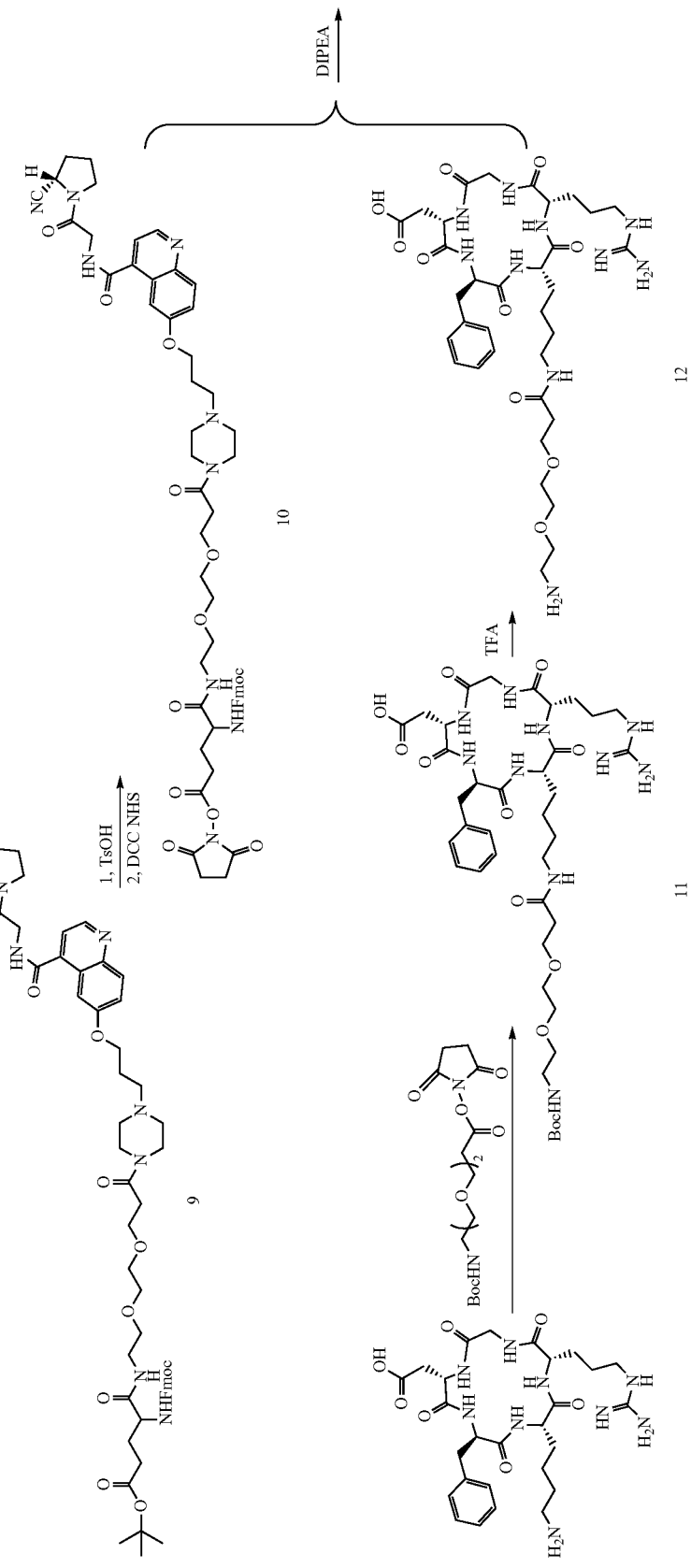

-continued
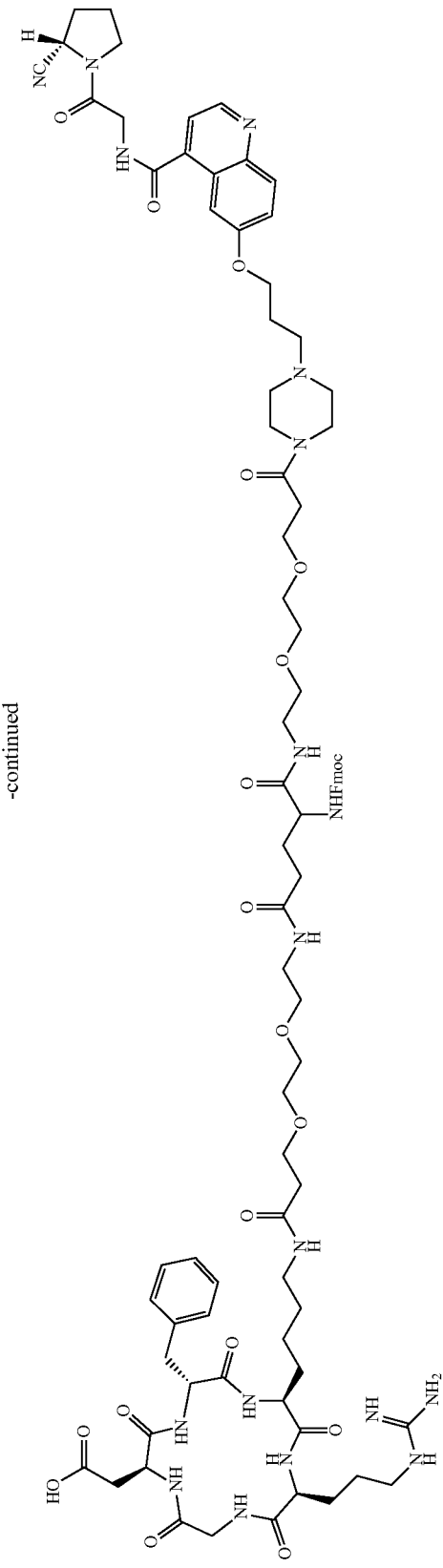
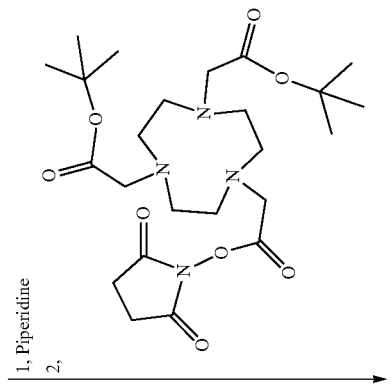
13 →
1, Piperidine
2,

-continued
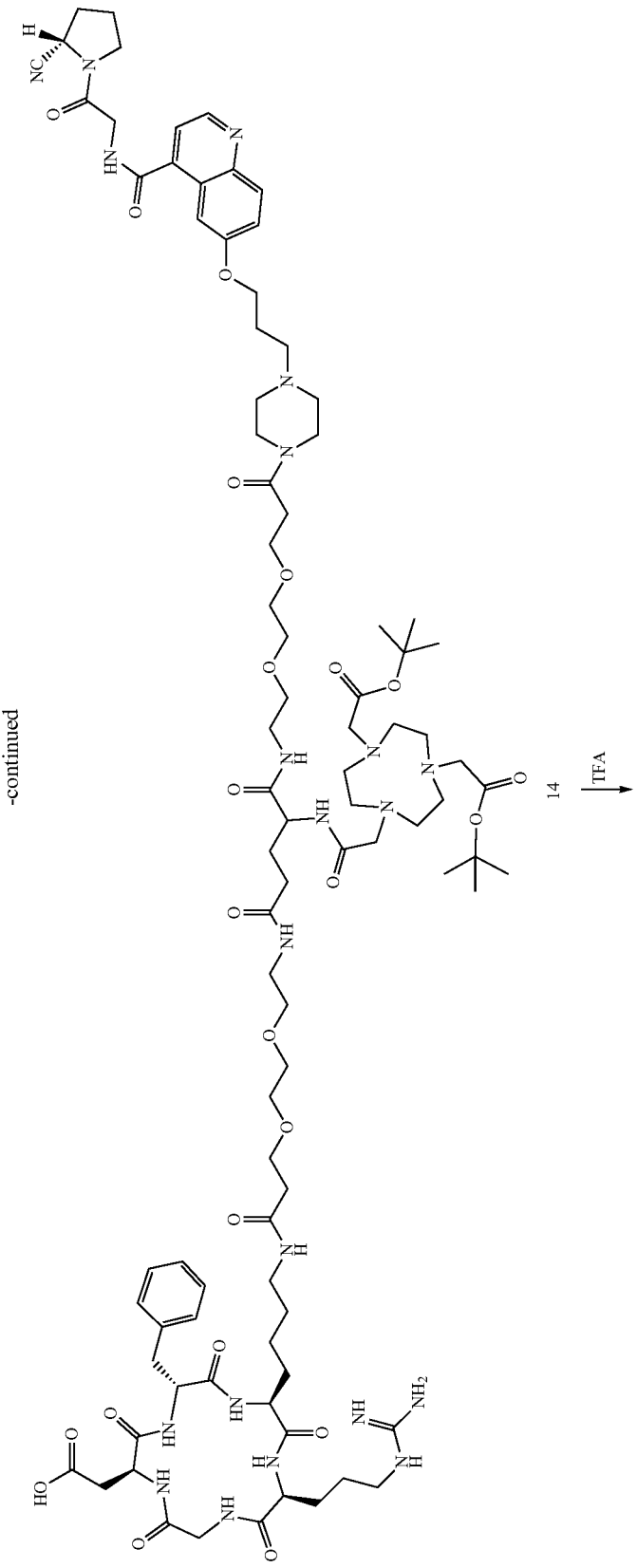

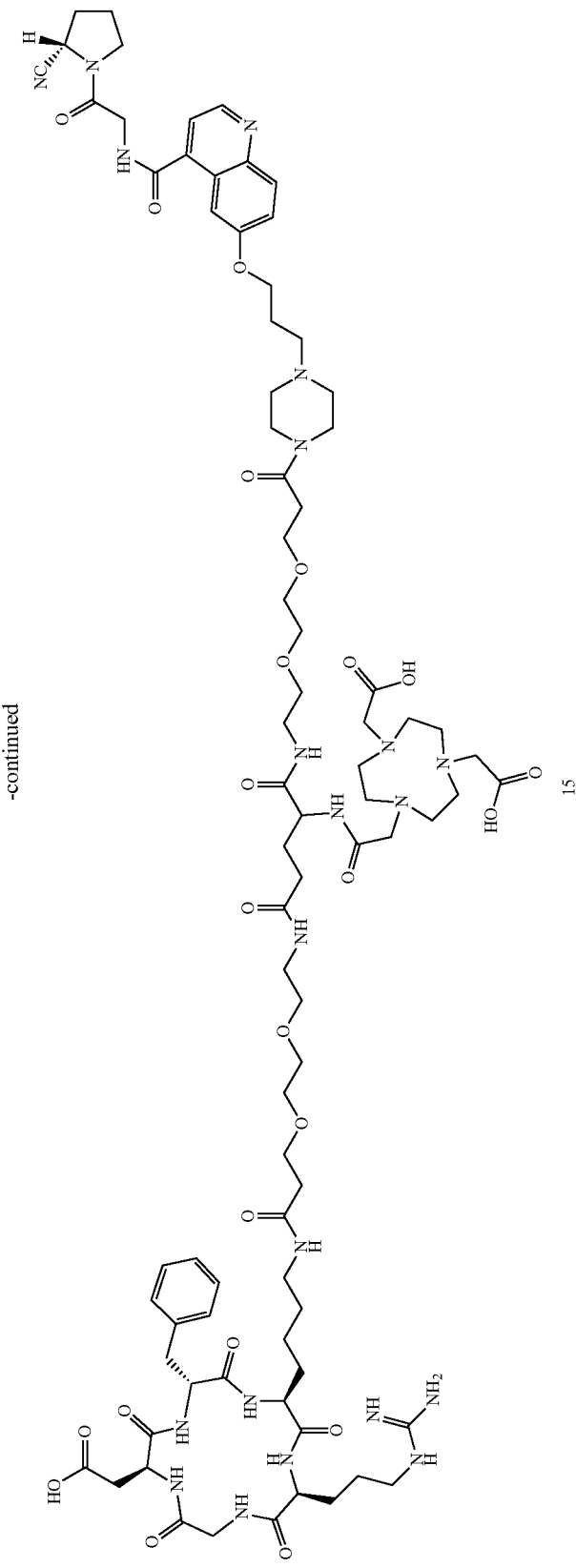

Example 2

The preparation method in Example 2 can refer to the preparation method in Example 1. The NOTA-2-tert-butyl-NHS-activated ester in the above example was substituted with NOTA-3-tert-butyl-NHS-activated ester to obtain the following structure:

Example 4: Preparation of a Radioactive $^{177}$Lu Labeled FAPI-RGD Complex ($^{177}$Lu-FAPI-RGD) Shown in Formula (I-2)

Preparation of a buffer solution with a pH of 5.5: 57.6 mg of acetic acid, 189 mg of gentianic acid and 525 mg of sodium acetate trihydrate were weighed and dissolved in 48

Formula (I-2)

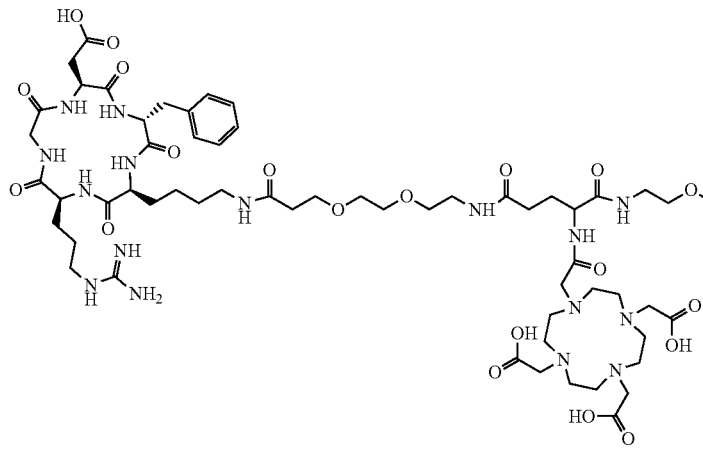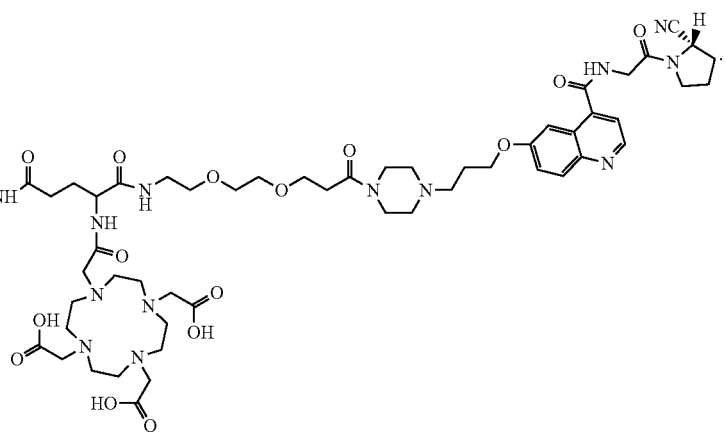

Example 3: Preparation of a Radioactive $^{68}$Ga Labeled FAPI-RGD Complex ($^{68}$Ga-FAPI-RGD) Shown in Formula (I-1)

Wet method: A hydrochloric acid solution of about 18.5-1,850 MBq of $^{68}$GaCl$_3$ (rinsed with a germanium-gallium generator) was added to an acetic acid-acetate solution (1.0 g/L) containing 0.5 mL of compound having the structure shown in Formula (I-1) prepared in Example 1 in a centrifuge tube, and a reaction was carried out at 37° C. for 20 min. A small C18 separation column was taken, slowly rinsed with 10 mL of anhydrous ethanol first, and then rinsed with 10 mL of water. The obtained labeled solution was diluted with 10 mL of water, and then sampled to the separation column. Unlabeled $^{68}$Ga ions were removed with 10 mL of water, and rinsing was conducted with 0.3 mL of 10 mM ethanol solution of HCl to obtain a $^{68}$Ga labeled FAPI-RGD complex. The rinsed solution was diluted with normal saline, followed by aseptic filtration to obtain injection of the $^{68}$Ga labeled FAPI-RGD complex.

Freeze-drying method: A hydrochloric acid solution of about 18.5-1,850 MBq of $^{68}$GaCl$_3$ (rinsed with a germanium-gallium generator) was added to a freeze-dried medicine box containing compound shown in Formula (I-1), and uniformly mixed for a reaction at 37° C. for 20 min. A small C18 separation column was taken, slowly rinsed with 10 mL of anhydrous ethanol first, and then rinsed with 10 mL of water. Resulting labeled solution was diluted with 10 mL of water, and then sampled to the separation column. Unlabeled $^{68}$Ga ions were removed with 10 mL of water, and rinsing was conducted with 0.3 mL of 10 mM ethanol solution of HCl to obtain rinsed solution of a complex. The rinsed solution was diluted with normal saline, followed by aseptic filtration to obtain an injection of the $^{68}$Ga labeled FAPI-RGD complex.

ml of pure water, and the pH was adjusted to 5.5 with a sodium hydroxide solution. 200 μg of compound having the structure shown in Formula (I-2) prepared in Example 2 was fully dissolved in 200 μL of the buffer solution (pH was 5.5), and then 5 ml of the buffer solution (pH was 5.5) and a hydrochloric acid solution of about 150 mCi of $^{177}$LuCl$_3$ were added. A mixture was shaken uniformly and heated for a reaction at 80° C. for 20 min. After the reaction was completed, cooling was conducted to room temperature. Then reaction solution was diluted with normal saline, followed by aseptic filtration to obtain an injection of 10 mCi/mL $^{117}$Lu labeled FAPI-RGD complex.

Experimental Example: Analysis and Application Effect

1. Analysis of the Stability of $^{68}$Ga Labeled FAPI-RGD Complex Shown in Formula (I-1)

Figure 10A:
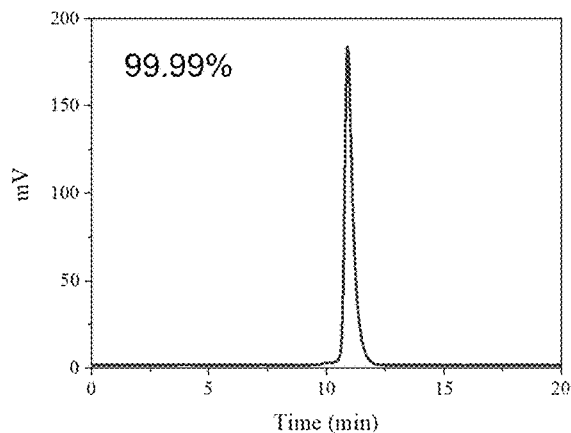
FIGS. 10A-10D are diagrams showing experimental results of the stability of $^{68}$Ga labeled FAPI-RGD complex shown in Formula (I-1) of the present disclosure in normal saline.
Figure 10B:
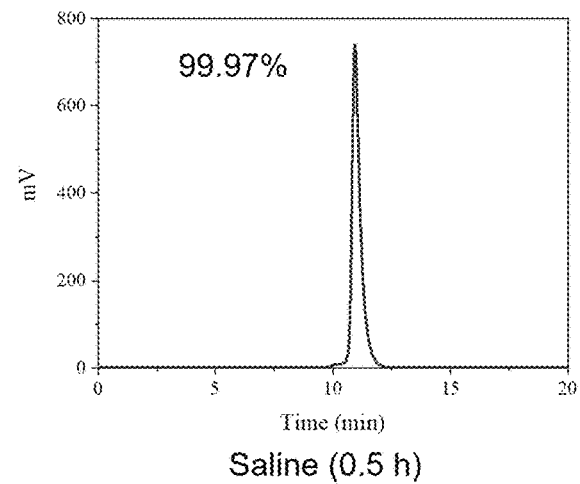
Figure 10C:
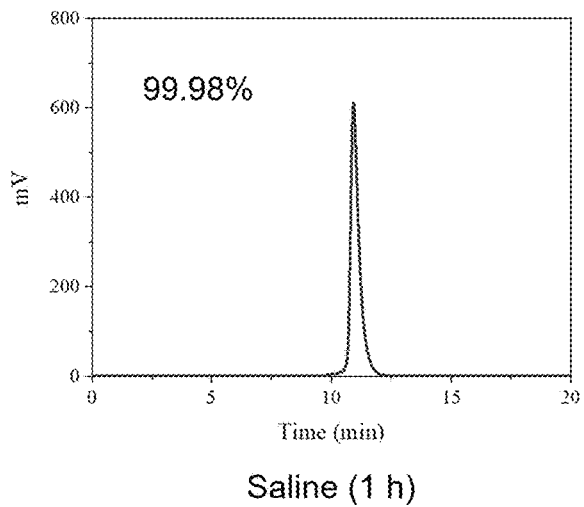
Figure 10D:
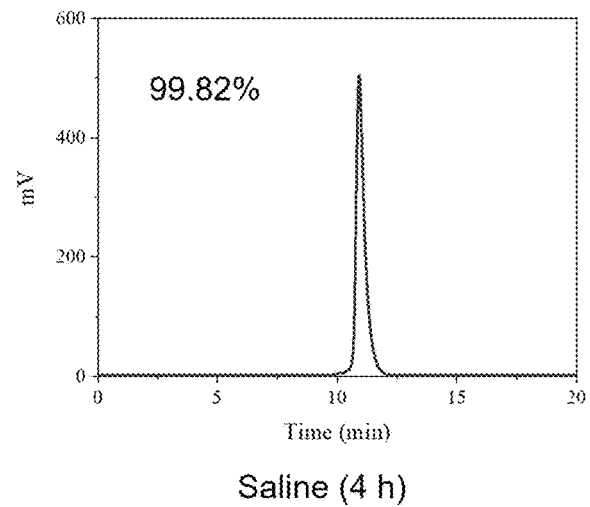

20 μL of a solution of $^{68}$Ga-FAPI-RGD (having an activity of 3.7 MBq/20 μL) prepared in Example 3 was added to a centrifuge tube containing 100 μL of normal saline or PBS (pH was 7.4) for co-incubation at 37° C. for 0.5 h, 1 h and 4 h to obtain co-incubation solution. 20 μL of the co-incubation solution was filtered with a 0.22 μm needle filter membrane, and then the radiochemical purity was analyzed by HPLC. Test results are shown in FIGS. 10A-10. After incubation in the normal saline, the $^{68}$Ga-FAPI-RGD is not obviously decomposed, and the radiochemical purity is greater than 99%, indicating that the $^{68}$Ga-FAPI-RGD prepared by the present disclosure has excellent stability.

2. Analysis of a Cell Experiment of the $^{68}$Ga Labeled FAPI-RGD Complex Shown in Formula (I-1)

Figure 11A:
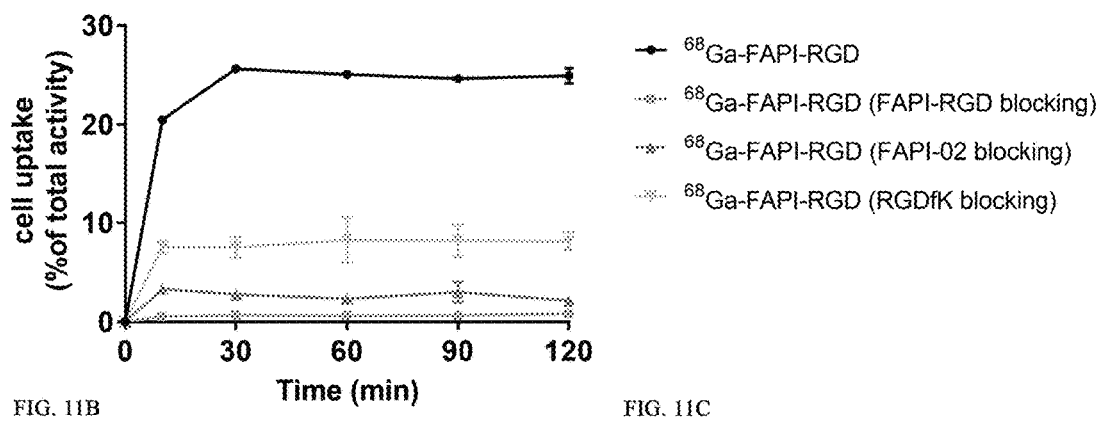
FIGS. 11A-11C are diagrams showing experimental results of cell uptake and cell binding of $^{68}$Ga labeled FAPI-RGD complex shown in Formula (I-1) of the present disclosure.
Figure 11B:
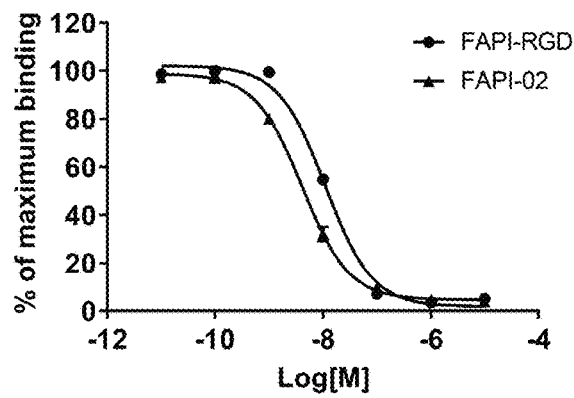
Figure 11C:
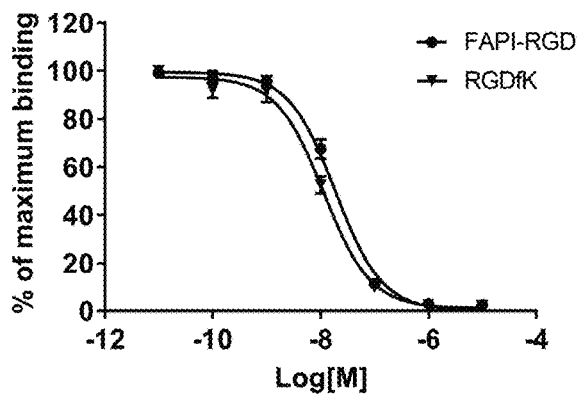

A cell uptake experiment of $^{68}$Ga-FAPI-RGD was carried out in HT1080-FAP tumor cells, and test results are shown in FIG. 11A. The $^{68}$Ga-FAPI-RGD has rapid cell uptake, and the maximum uptake is reached after incubation for 30 min and remained at similar uptake level for 2 h. In addition, it is proven by a blocking experiment that the cell uptake of the $^{68}$Ga-FAPI-RGD can be partially inhibited by C(RGDfK) or FAPI-02, and can be completely blocked by FAPI-RGD (with reference to FIG. 11A. A cell binding experiment was carried out in HT1080-FAP and U87MG tumor cells, and test results are shown in FIGS. 11B and 11C, respectively. According to the cell experiment of HT1080-FAP, the $IC_{50}$ value of $^{68}$Ga-FAPI-RGD and $^{68}$Ga-FAPI-02 was 11.17 nM and 4.14 nM, respectively after measurement. According to the cell experiment of HT1080-FAP, the $IC_{50}$ value of $^{68}$Ga-FAPI-RGD and $^{68}$Ga-C(RGDfK) was 18.93 nM and 11.49 nM, respectively after measurement. The experimental results show that compared with corresponding monomers, the FAPI-RGD has similar affinity for corresponding receptors FAP and integrin $\alpha_v\beta_3$.

Figure 12A:
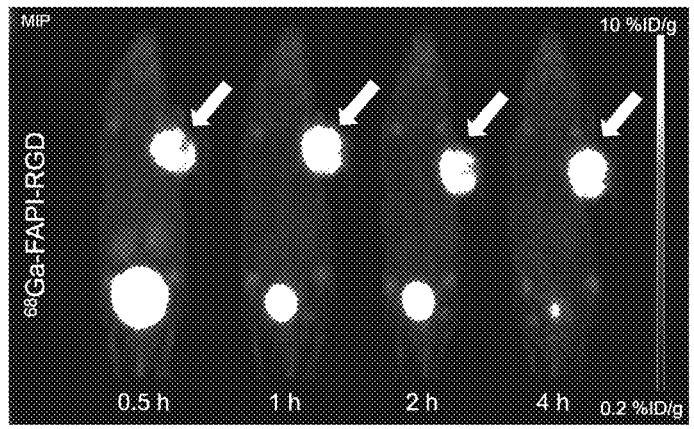
FIGS. 12A-12F are diagrams showing MicroPET imaging results of $^{68}$Ga labeled FAPI-RGD complex shown in Formula (I-1) of the present disclosure and monomers $^{68}$GA-FAPI-02 and $^{68}$Ga-C(RGDfK) in HT1080-FAP tumor-bearing mice.
Figure 12B:
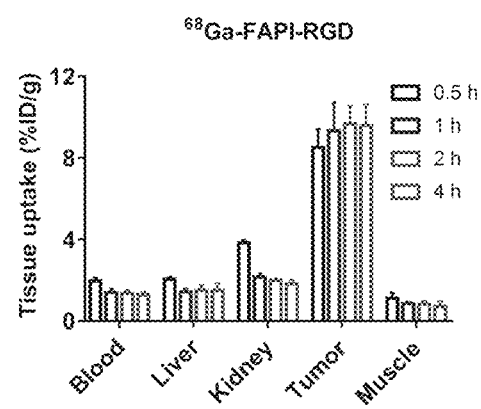
Figure 12C:
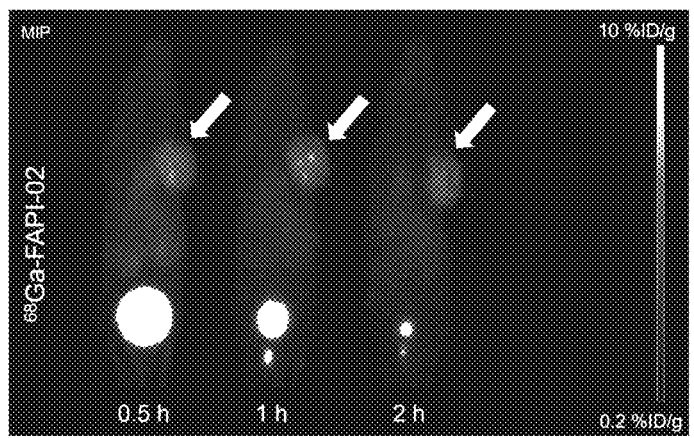
Figure 12D:
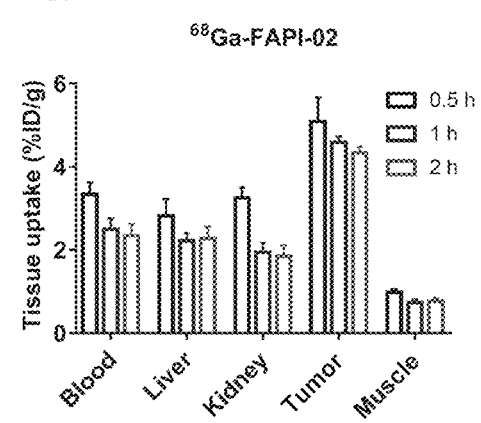
Figure 12E:
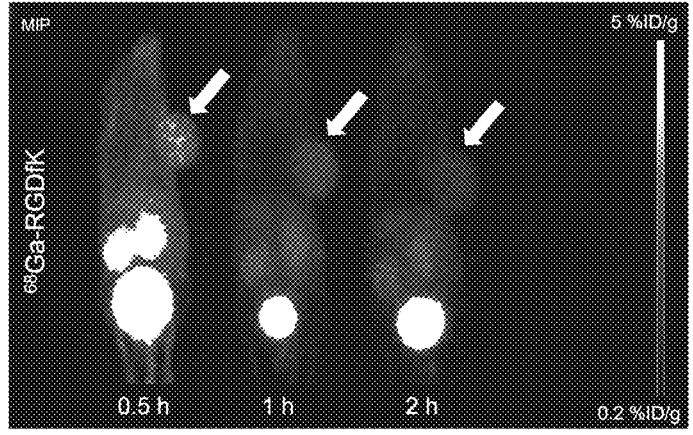
Figure 12F:
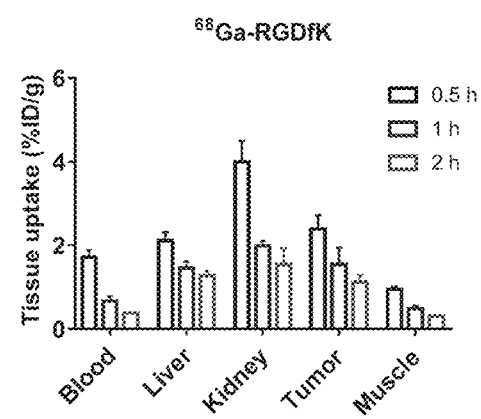
Figure 13A:
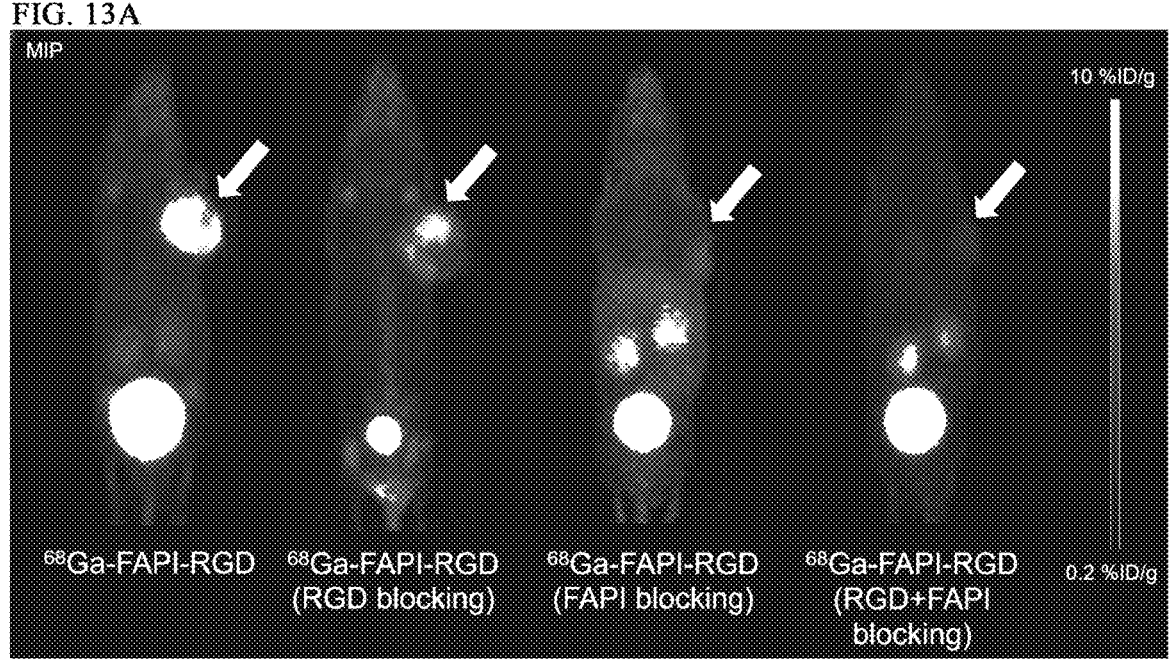
FIGS. 13A-13C are diagrams showing MicroPET imaging results and statistics of uptake results in tumors and vital organs 30 min after co-injection of $^{68}$Ga labeled FAPI-RGD complex shown in Formula (I-1) of the present disclosure and C(RGDfK) and/or FAPI-02.
Figure 13B:
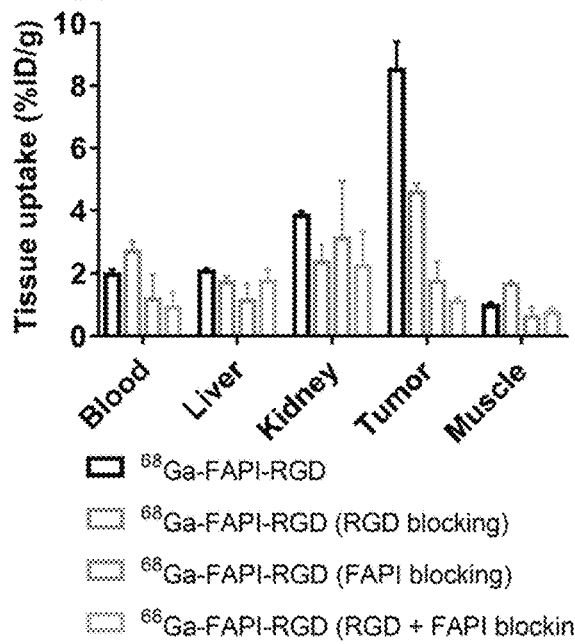
Figure 13C:
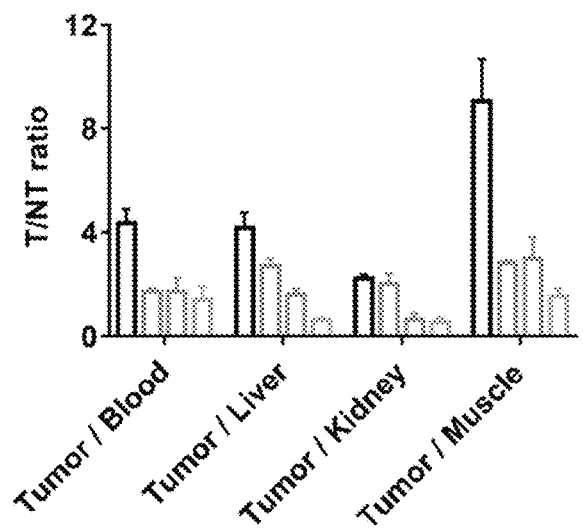

3. MicroPET Imaging of $^{68}$Ga Labeled FAPI-RGD Complex Shown in Formula (I) in Tumor-Bearing Mice $^{68}$Ga-FAPI-RGD was prepared according to the method in Example 3. 7.4 MBq of the $^{68}$Ga-FAPI-RGD, $^{68}$Ga-FAPI-02 and $^{68}$Ga-C(RGDfK) were intravenously injected into tails of HT1080-FAP tumor-bearing mice which were randomly divided into groups, and after anaesthetization with isoflurane, MicroPET imaging was conducted on the $^{68}$Ga-FAPI-RGD group after administration for 0-240 min and on the other groups after administration for 0-120 min. Results are shown in FIGS. 12A-12F FIGS. 12A, 12C and 12E show maximum-density MicroPET projection images of HT1080-FAP tumor-bearing mice (n was 3) at different time points after intravenous injection in the above three groups of mice, respectively. FIGS. 12B, 12D and 12F show the uptake in various organs or tissues (including blood, liver, kidneys, tumors and muscles) of the above three groups of mice at different time points after injection, respectively. Three dose uptakes in each group from left to right correspond to 0.5 h, 1 h and 2 h after injection, respectively. FIGS. 12A-12F show that tumors are clearly visible at the time points of imaging acquisition, and the $^{68}$Ga-FAPI-RGD has higher uptake in tumors than the monomers $^{68}$Ga-FAPI-02 and $^{68}$Ga-C(RGDfK). A specific binding property of the $^{68}$Ga-FAPI-RGD to integrin $\alpha_v\beta_3$ and FAP in vivo is confirmed by a blocking experiment. The above $^{68}$Ga-FAPI-RGD and C(RGDfK) or FAPI-02 were co-injected into HT1080-FAP tumor-bearing mice. MicroPET imaging results and organ uptake results are shown in FIGS. 13A-13C. In FIG. 13A, the four images correspond to images obtained after single injection of $^{68}$Ga-FAPI-RGD, co-injection of $^{68}$Ga-FAPI-RGD and C(RGDfK), co-injection of $^{68}$Ga-FAPI-RGD and FAPI-02, and co-injection of $^{68}$Ga-FAPI-RGD, C(RGDfK) and FAPI-02 from left to right, respectively. FIGS. 13B and 13C respectively show the uptake of $^{68}$Ga-FAPI-RGD in various organs or tissues (including blood, liver, kidneys, tumors and muscles) and the target/non-target ratio of mice, after injection in different way of the above four groups. Four bar graphs for each organ or tissue in FIGS. 13B and 13C correspond to the four injection ways in FIG. 13A from left to right, respectively. From FIGS. 13A-13C, it can be seen that after co-injection of the $^{68}$Ga-FAPI-RGD and RGD or FAPI-02, the uptake of the $^{68}$Ga-FAPI-RGD in tumors can be reduced, and after co-injection of the $^{68}$Ga-FAPI-RGD, C(RGDfK) and FAPI-02, the uptake of the $^{68}$Ga-FAPI-RGD in tumors is further reduced. It is proven by a clocking experiment that the $^{68}$Ga-FAPI-RGD can achieve specific targeting of tumors by binding to integrin $\alpha_v\beta_3$ and FAP in vivo.

4. SEPCT Imaging of $^{177}$Lu Labeled FAPI-RGD Complex Shown in Formula (II) in Tumor-Bearing Mice $^{177}$Lu-FAPI-RGD was prepared according to the method in Example 4. 37 MBq of the $^{177}$Lu-FAPI-RGD was intravenously injected into tails of HT1080-FAP tumor-bearing mice, and after anaesthetization with isoflurane, SPECT imaging was conducted after administration for 4 h. Results are shown in FIG. 14. It can be seen that tumors are clearly visible after 4 h of administration.

5. MicroPET Imaging of Complex of $^{68}$Ga Labeled FAPI-RGD (Control Compound) in Tumor-Bearing Mice As a control, a thiosuccinimide bond formed by maleimide and mercaptan was used as a connecting structure, compound shown in FIG. 15B was prepared, labeling with $^{68}$Ga was conducted according to the method in Example 3, and MicroPET imaging study was carried out in HT1080-FAP tumor-bearing mice. Results are shown in FIGS. 15A and 15C. FIG. 15A shows that at the time points of imaging acquisition, major radioactive signals are concentrated in the liver and kidneys, and less uptake in tumors is achieved. FIG. 15C also shows high uptake in the liver and kidneys and low uptake in tumors. Therefore, when the thiosuccinimide bond is used as a connecting structure, the affinity of targeting group to targeted receptor may be reduced, leading to decrease of the uptake in target organ. Meanwhile, the uptake in non-target tissues is too high, leading to decrease of the target/non-target ratio, so that adverse reactions are more likely to be caused. A specific connecting structure of the present disclosure can not only ensure high affinity for receptor but also provide suitable pharmacokinetic properties, so that high absolute uptake in tumors and high target/non-target ratio are ensured.

Figure 16:
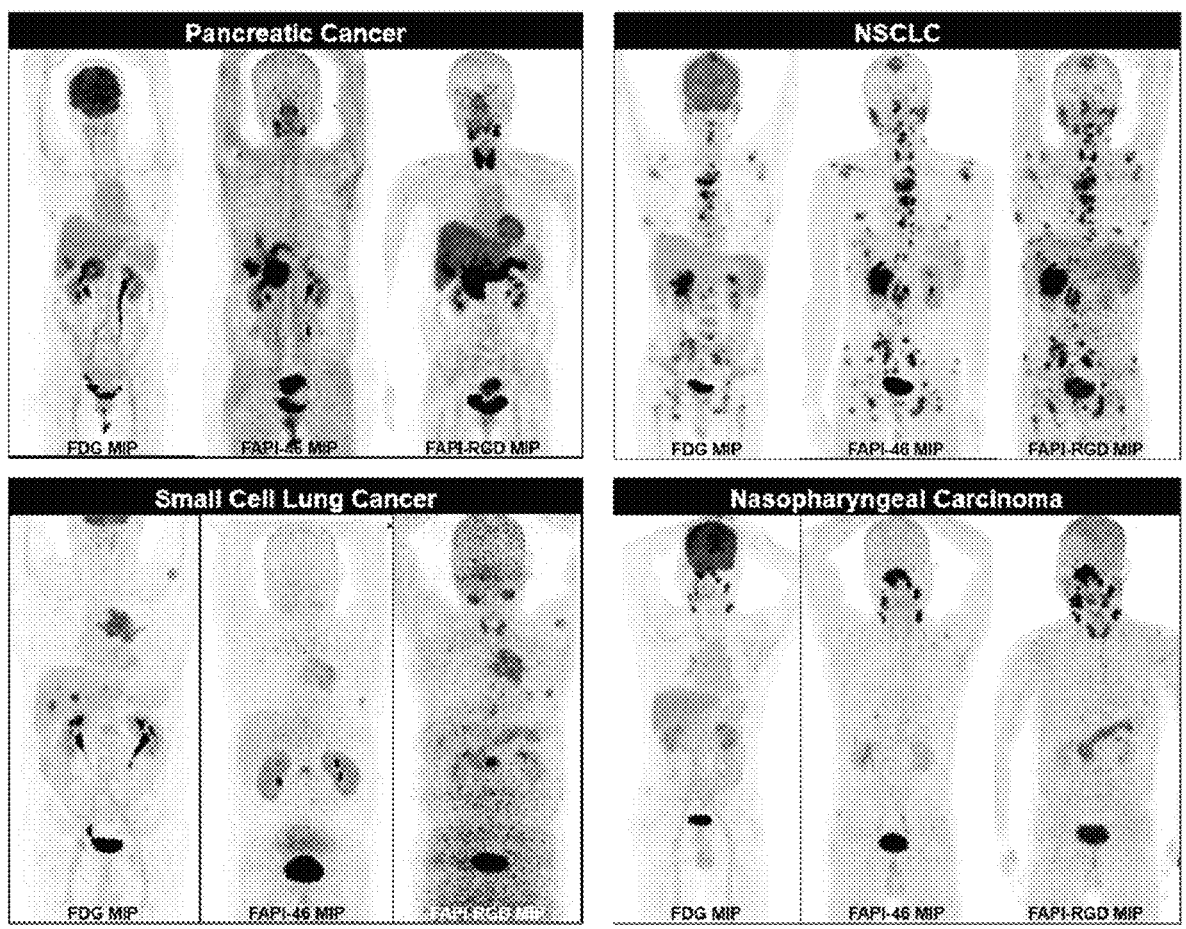
FIG. 16 is a diagram showing PET/CT imaging results 3 h after $^{68}$Ga labeled FAPI-RGD complex shown in Formula (I-1) of the present disclosure, $^{18}$F-FDG and $^{68}$Ga-FAPI46 are intravenously injected into patients with pancreatic cancer, non-small cell lung cancer, small cell lung cancer and nasopharyngeal carcinoma.

6. PET/CT Imaging of a $^{68}$Ga Labeled FAPI-RGD Complex Shown in Formula (I-1) in Patients with Tumors $^{68}$Ga-FAPI-RGD clinical trial was approved by the Clinical Research Ethics Committee of the First Affiliated Hospital of Xiamen University. All subjects, including a patient with pancreatic cancer, a patient with non-small cell lung cancer, a patient with small cell lung cancer and a patient with nasopharyngeal cancer, signed a written informed consent. The dose of intravenous injection of $^{68}$Ga-FAPI-RGD was calculated based on the body weight of every subject (1.8-2.2 MBq [0.05-0.06 mCi]/kg). A hybrid PET/CT scanner (Discovery MI, GE Healthcare, Milwaukee, WI, USA) was used to obtain data 3 h after the intravenous injection. Imaging results are shown in FIG. 16. The maximum standard uptake value ($SUV_{max}$) was calculated automatically by using the region of interest (ROI) drawn on a longitude image. The $SUV_{max}$ of the $^{68}$Ga-FAPI-RGD targeting dual targets in different types of tumors is higher than that of $^{68}$Ga-FAPI-46 targeting single FAP target, and the $SUV_{max}$ is increased by about 30-50%, proving that the design of targeting dual targets can improve the number of effective receptors in tumors and the utilization efficiency so as to improve the uptake in tumors.

In summary, an FAPI-RGD structure is developed by the present disclosure. The compound has high affinity for the FAP target and the integrin $\alpha_v\beta_3$ target, can realize synergistic targeting of the FAP target and the integrin $\alpha_v\beta_3$ target in tumors, has excellent pharmacokinetics, high uptake in tumors and long retention time in tumors, and is expected to be applied to diagnosis or therapy of diseases characterized by overexpression of FAP and/or integrin $\alpha_v\beta_3$.

Although the present disclosure has been described in detail by general descriptions, specific embodiments and tests above, it is obvious to persons skilled in the field that some modifications or improvements can be made on the basis of the present disclosure. Therefore, all the modifications or improvements made without departing from the spirit of the present disclosure shall fall within the protection scope of the present disclosure.

The invention claimed is:
1. A dual-targeting compound, wherein the compound structurally contains ligand structures specifically binding to FAP and integrin $\alpha_v\beta_3$ at the same time, and the compound has the following structure shown in Formula (I):

(I)

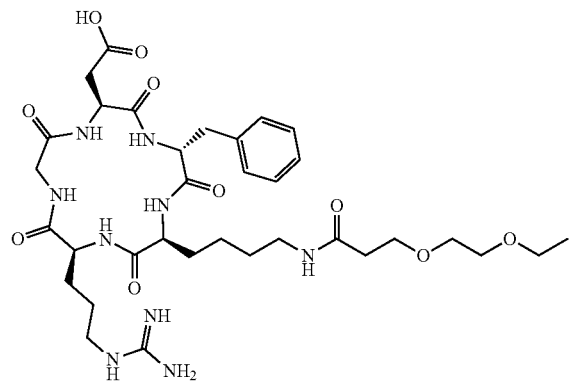

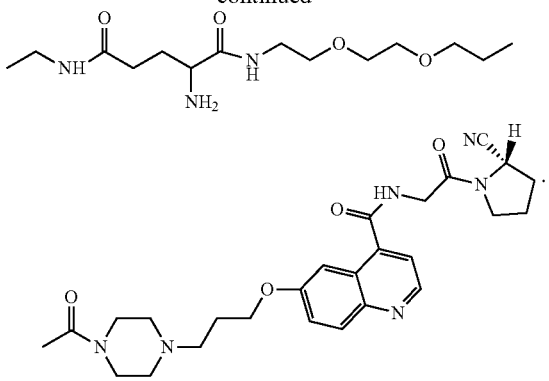

2. A dual-targeting compound capable of being labeled with a radionuclide, wherein the compound structurally contains ligands specifically binding to FAP and integrin $\alpha_v\beta_3$ at the same time and a nuclide chelating structure, and the compound has the following structure shown in Formula (I-1) or Formula (I-2):

(I-1)

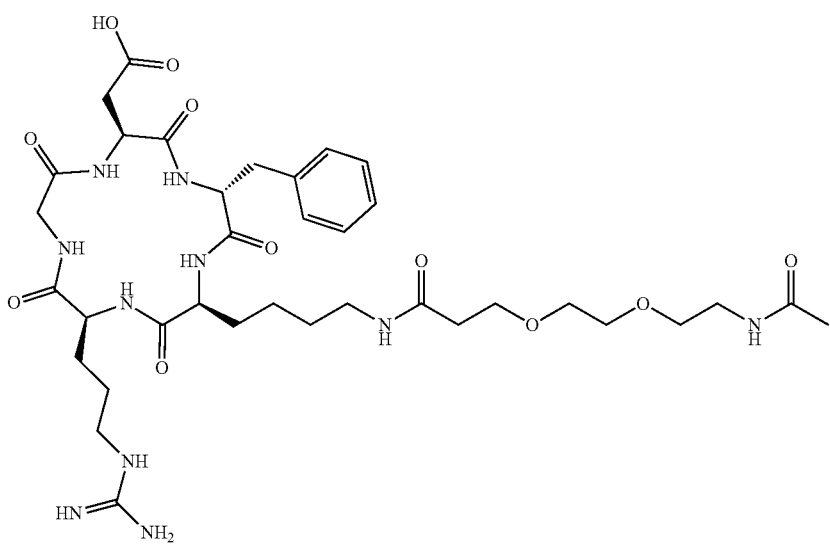

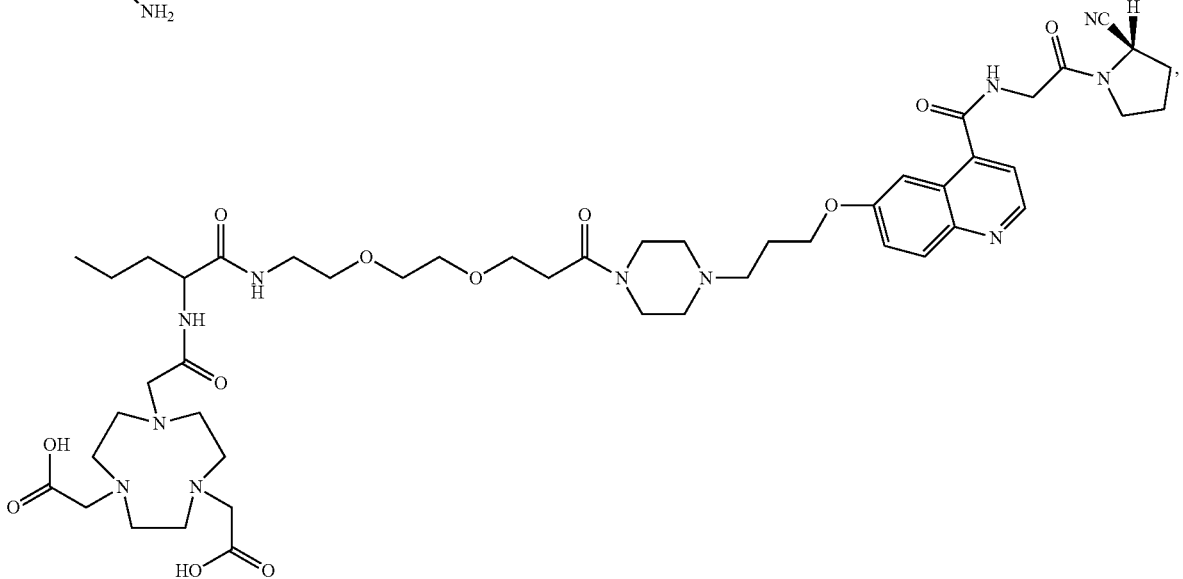

-continued (I-2)

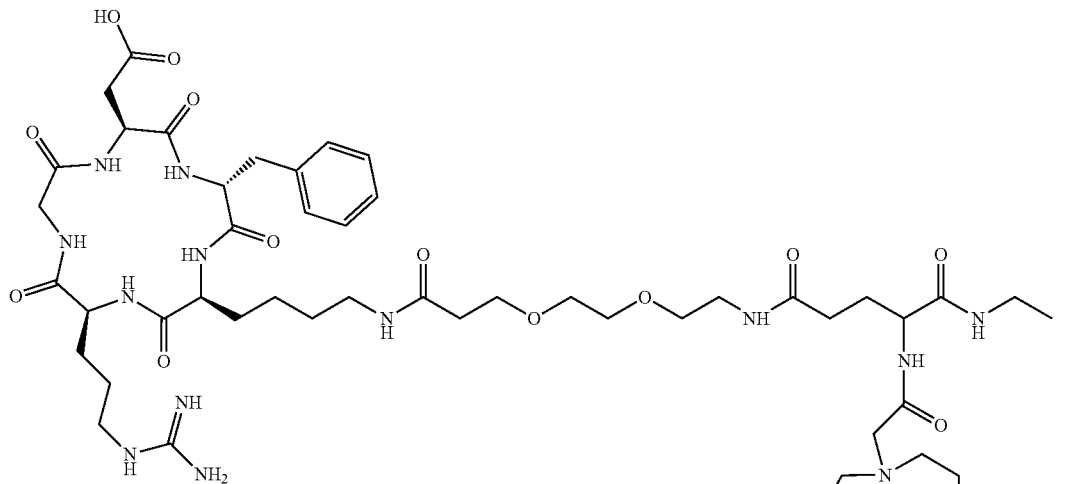

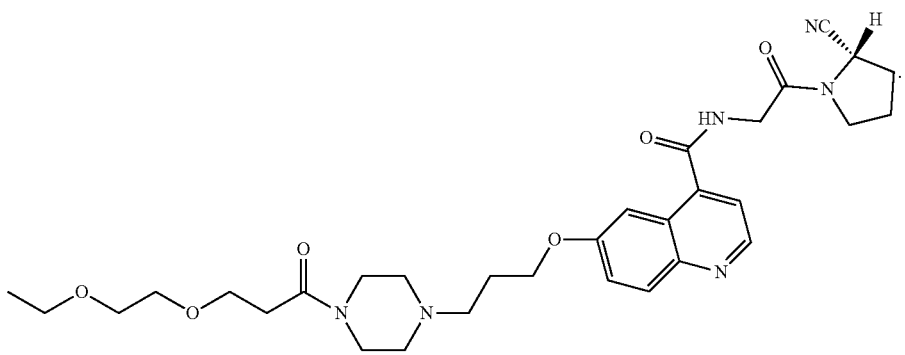

3. A method for preparing the dual-targeting compound capable of being labeled with a radionuclide according to claim 2, comprising the following steps: (i) reacting 6-hydroxyquinoline-4-carboxylic acid with amino of tert-butyl glycinate by amide condensation to obtain Compound 2; (ii) reacting Compound 2 and 1-bromo-3-chloropropane to obtain Compound 3: (iii) reacting Compound 3 and tert-butyl 1-piperazinecarboxylate to obtain Compound 4 (iv) removing a Boc protective group and a tert-butyl protective group from Compound 4 under acidic conditions to obtain Compound 5, and introducing a Boc protective group to piperazine ring of Compound 5, followed by an amide condensation reaction with (S)-pyrrolidene-2-carbonitrile hydrochloride; (v) removing the Boc protective group, carrying out a condensation reaction with N-Boc-3-[2-(2-aminoethoxy)ethoxy]propionic acid; (vi) removing the Boc protective group, and carrying out a reaction with Fmoc-O-tert-butyl-L-glutamic acid to obtain Compound 9; (vii) reacting Compound 9 with p-toluenesulfonic acid monohydrate, followed by a reaction with DCC and NHS to obtain Intermediate 10, c(RGDfK) with amino-dipolyethylene glycol to obtain Compound 11 and remove the Boc to obtain Compound 12, followed by reacting Intermediate 10 and Compound 12 to obtain a dual-targeting compound; (viii) removing an Fmoc protective group and then carrying out a reaction with a nuclide chelating agent, wherein the nuclide chelating agent is 1,4,7,10-tetraazacyclododecane-N,N',N,N'-tetraacetic acid or 1,4,7-triazacyclononane-1,4,7-triacetic acid; and (ix) removing a tert-butyl protective group on a chelating group to obtain a dual-targeting compound capable of being labeled with a radionuclide, wherein Compound 2 has the following Formula (II):
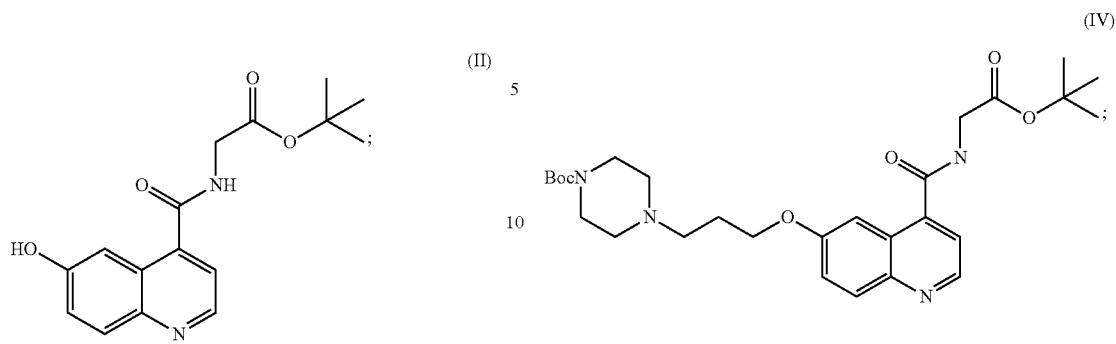
wherein Compound 3 has the following Formula (III):
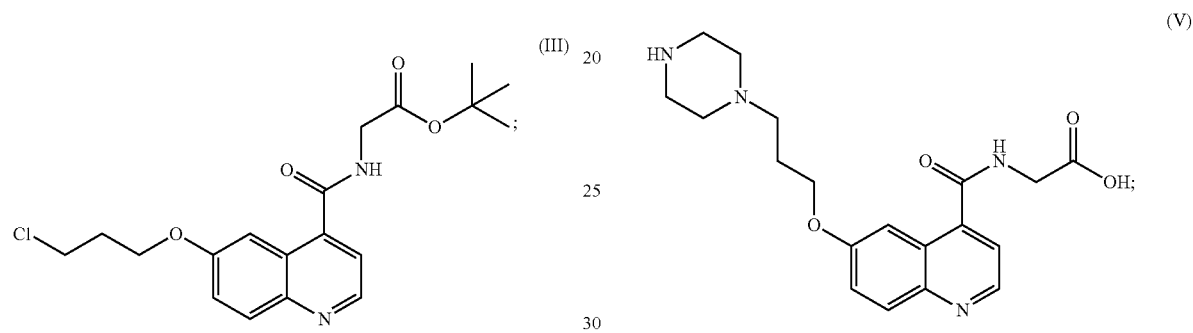
wherein Compound 4 has the following Formula (IV):
wherein Compound 5 has the following Formula (V):
wherein Compound 9 has the following Formula (IX):
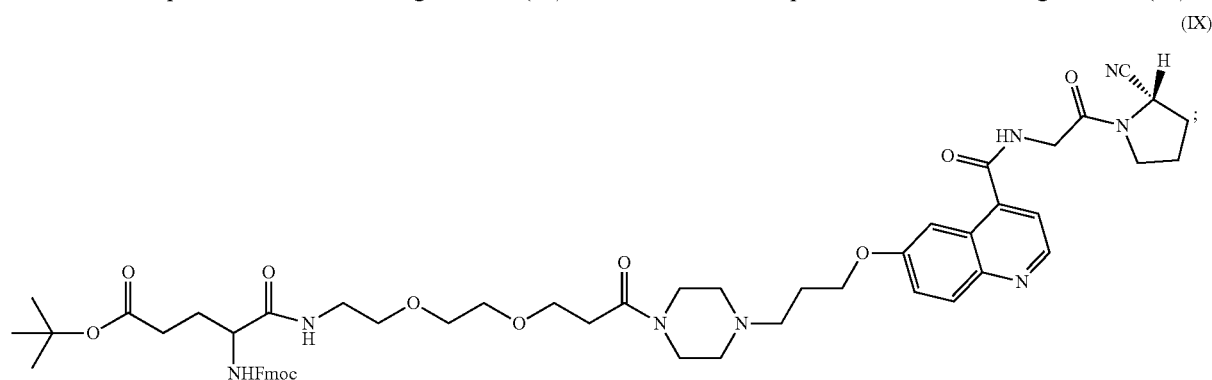
wherein Intermediate 10 has the following Formula (X):
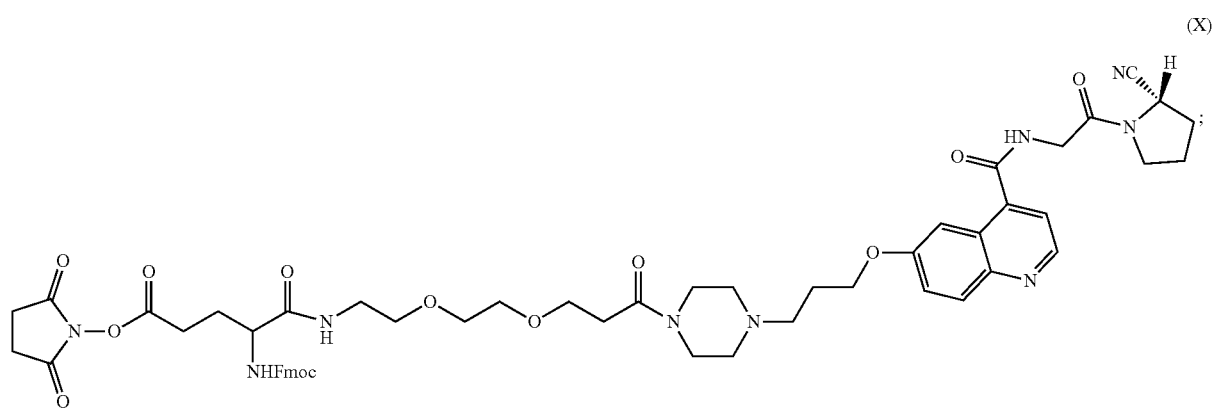

wherein Compound 12 has the following Formula (XII)

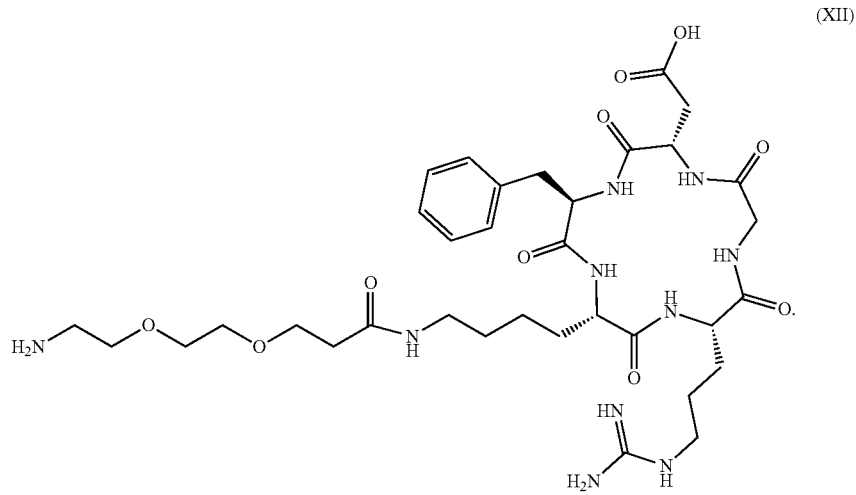 [SMILES: N=C(N)NCCC[C@@H]1NC(=O)[C@H](CCCCNC(=O)CCOCCOCCN)NC(=O)[C@@H](Cc2ccccc2)NC(=O)[C@H](CC(=O)O)NC(=O)CNC1=O]

4. A radionuclide labeled dual-targeting compound, comprising the dual-targeting compound capable of being labeled with a radionuclide according to claim 2 and a radionuclide; and the radionuclide is selected from an α-ray emitting isotope, a β-ray emitting isotope, a γ-ray emitting isotope, an auger electron emitting isotope, or an X-ray emitting isotope.

5. The radionuclide labeled dual-targeting compound according to claim 4, wherein the radionuclide is selected from any one of $^{18}F$, $^{51}Cr$, $^{67}Ga$, $^{68}Ga$, $^{111}In$, $^{99m}Tc$, $^{186}Re$, $^{188}Re$, $^{139}La$, $^{140}La$, $^{175}Yb$, $^{153}Sm$, $^{166}Ho$, $^{86}Y$, $^{90}Y$, $^{149}Pm$, $^{165}Dy$, $^{169}Er$, $^{177}Lu$, $^{47}Sc$, $^{142}Pr$, $^{159}Gd$, $^{212}Bi$, $^{213}Bi$, $^{72}As$, $^{72}Se$, $^{97}Ru$, $^{109}Pd$, $^{105}Rh$, $^{105}Rh$, $^{101m}Rh$, $^{119}Sb$, $^{128}Ba$, $^{123}I$, $^{124}I$, $^{131}I$, $^{197}Hg$, $^{159}Gd$, $^{212}Bi$, $^{213}Bi$, $^{72}As$, $^{72}Se$, $^{97}Ru$, $^{109}Pd$, $^{105}Rh$, $^{101m}Rh$, $^{119}Sb$, $^{128}Ba$, $^{123}I$, $^{124}I$, $^{131}I$, $^{197}Hg$, $^{211}At$, $^{151}Eu$, $^{153}Eu$, $^{169}Eu$, $^{201}Tl$, $^{203}Pb$, $^{212}Pb$, $^{64}Cu$, $^{67}Cu$, $^{198}Au$, $^{225}Ac$, $^{227}Th$, $^{89}Zr$, or $^{199}Ag$.

6. The radionuclide labeled dual-targeting compound according to claim 4, wherein the radionuclide is selected from $^{18}F$, $^{64}Cu$, $^{68}Ga$, $^{89}Zr$, $^{90}Y$ $^{111}In$, $^{99m}Tc$, $^{177}Lu$, $^{188}Re$, or $^{225}Ac$.

7. A method for preparing a radionuclide labeled dual-targeting compound, wherein the radionuclide labeled dual-targeting compound is obtained by labeling any one of the dual-targeting compounds capable of being labeled with a radionuclide according to claim 2 with a radionuclide; and the radionuclide is selected from an α-ray emitting isotope, a β-ray emitting isotope, a γ-ray emitting isotope, an auger electron emitting isotope, or an X-ray emitting isotope; the method comprising: reacting the dual-targeting compound capable of being labeled with a radionuclide according to claim 2 with a radionuclide by wet labeling or freeze-drying labeling to obtain the radionuclide labeled dual-targeting compound.

8. A pharmaceutical composition, comprising the radionuclide labeled dual-targeting compound according to claim 4, or a pharmaceutically acceptable hydrate, solvate or salt thereof.

9. A method of diagnosing or treating a disease characterized by overexpression of at least one selected from the group consisting of FAP and integrin $α_vβ_3$, comprising: administering, to a subject in need thereof, an effective amount of the dual-targeting compound according to claim 1, or a pharmaceutically acceptable hydrate, solvate or salt thereof, comprising a radionuclide.

10. A method of diagnosing or treating a disease characterized by overexpression of at least one selected from the group consisting of FAP and integrin $α_vβ_3$, comprising: administering, to a subject in need thereof, an effective amount of the dual-targeting compound capable of being labeled with a radionuclide according to claim 2, or a pharmaceutically acceptable hydrate, solvate or salt thereof, comprising a radionuclide.

11. A method of diagnosing or treating a disease characterized by overexpression of at least one selected from the group consisting of FAP and integrin $α_vβ_3$, comprising: administering, to a subject in need thereof, an effective amount of the radionuclide labeled dual-targeting compound according to claim 4, or a pharmaceutically acceptable hydrate, solvate or salt thereof.

12. A method of diagnosing or treating a disease characterized by overexpression of at least one selected from the group consisting of FAP and integrin $α_vβ_3$, comprising: administering, to a subject in need thereof, an effective amount of the pharmaceutical composition according to claim 8.

13. The method according to claim 9, wherein the disease characterized by overexpression of at least one selected from the group consisting of FAP and integrin $α_vβ_3$ comprises cancer, chronic inflammation, atherosclerosis, or cicatricial diseases.

14. The method according to claim 13, wherein the cancer is selected from breast cancer, pancreatic cancer, small bowel cancer, colon cancer, rectal cancer, lung cancer, head and neck cancer, ovarian cancer, hepatocellular carcinoma, esophageal cancer, hypopharyngeal cancer, nasopharyngeal cancer, laryngeal cancer, myeloma cells, bladder cancer, cholangiocellular carcinoma, clear cell renal cell carcinoma, neuroendocrine carcinoma, carcinogenic osteomalacia, sarcoma, cancer of unknown primary, thymic carcinoma, glioma, neuroglioma, astrocytoma, cervical cancer, and prostate cancer.

* * * * *